(12) United States Patent
Cohen et al.

(10) Patent No.: US 9,789,098 B2
(45) Date of Patent: Oct. 17, 2017

(54) NOOTROPIC COMPOSITIONS FOR IMPROVING MEMORY PERFORMANCE

(71) Applicant: Pharnext, Issy les Moulineaux (FR)

(72) Inventors: Daniel Cohen, Saint Cloud (FR); Serguei Nabirochkin, Chatenay Malabry (FR); Ilya Chumakov, Vaux le Penil (FR)

(73) Assignee: PHARNEXT, Issy les Moulineaux (FR)

( * ) Notice: Subject to any disclaimer, the term of this patent is extended or adjusted under 35 U.S.C. 154(b) by 125 days.

(21) Appl. No.: 14/425,987

(22) PCT Filed: Sep. 4, 2013

(86) PCT No.: PCT/EP2013/068302
§ 371 (c)(1),
(2) Date: Mar. 4, 2015

(87) PCT Pub. No.: WO2014/037412
PCT Pub. Date: Mar. 13, 2014

(65) Prior Publication Data
US 2015/0224092 A1    Aug. 13, 2015

Related U.S. Application Data

(60) Provisional application No. 61/696,961, filed on Sep. 5, 2012.

(30) Foreign Application Priority Data

Sep. 5, 2012  (EP) .................................... 12306062

(51) Int. Cl.
| | | |
|---|---|---|
| A61K 31/197 | (2006.01) | |
| A61K 31/42 | (2006.01) | |
| A61K 45/06 | (2006.01) | |
| A61K 31/44 | (2006.01) | |
| A61K 31/135 | (2006.01) | |
| A61K 31/137 | (2006.01) | |
| A61K 31/185 | (2006.01) | |
| A61K 31/195 | (2006.01) | |
| A61K 31/635 | (2006.01) | |
| A61K 31/138 | (2006.01) | |
| A61K 31/16 | (2006.01) | |

(52) U.S. Cl.
CPC ............ *A61K 31/44* (2013.01); *A61K 31/135* (2013.01); *A61K 31/137* (2013.01); *A61K 31/138* (2013.01); *A61K 31/16* (2013.01); *A61K 31/185* (2013.01); *A61K 31/195* (2013.01); *A61K 31/197* (2013.01); *A61K 31/42* (2013.01); *A61K 31/635* (2013.01); *A61K 45/06* (2013.01)

(58) Field of Classification Search
None
See application file for complete search history.

(56) References Cited

FOREIGN PATENT DOCUMENTS

| WO | WO 2009/070583 | 6/2009 |
|---|---|---|
| WO | WO 2009/133128 | 11/2009 |
| WO | WO 2009/133141 | 11/2009 |
| WO | WO 2010/138833 | 12/2010 |
| WO | WO 2012/117073 | 9/2012 |
| WO | WO 2012/117075 | 9/2012 |
| WO | WO 2012/117076 | 9/2012 |
| WO | WO 2013/127918 | 9/2013 |

OTHER PUBLICATIONS

Fan et. al., Bioorganic & Medicinal Chem. Letters, 1997, 7(24): 3107-3112.*
Hudkins et. al., Bioorganic and Medicinal Chemistry Letters, 8, pp. 1873-1876, (1998).*
Van Sickle et. al., Lipids, 27(3), pp. 157-160, (1992).*

* cited by examiner

*Primary Examiner* — Svetlana M Ivanova
(74) *Attorney, Agent, or Firm* — Browdy and Neimark, PLLC

(57) ABSTRACT

The invention relates to compositions and methods for improving memory and related functions as alertness, attention, concentration, learning, and language processing. More particularly, the invention relates to compositions comprising at least two drugs selected from cinacalcet, baclofen, acamprosate, mexiletine, sulfisoxazole and torasemide useful to enhance memory and related functions in healthy subjects or subjects suffering from conditions or disorders having a negative impact on their memory.

12 Claims, 10 Drawing Sheets

NOOTROPIC COMPOSITIONS FOR IMPROVING MEMORY PERFORMANCE

RELATED APPLICATIONS

This application is a national stage filing under 35 U.S.C. §371 of International Application PCT/EP2013/068302 entitled "NOOTROPIC COMPOSITIONS FOR IMPROVING MEMORY PERFORMANCE," filed Sep. 4, 2013, which claims priority to EP Application No. 12306062.6, filed Sep. 5, 2012, and claims the benefit of U.S. provisional application 61/696,961, filed Sep. 5, 2012. Each of prior application is incorporated by reference herein in its entirety.

FIELD OF THE INVENTION

The present invention relates to nootropic compositions and the uses thereof, e.g., to stimulate cognition. More particularly, the invention provides novel compositions comprising at least two drugs selected form cinacalcet, baclofen, acamprosate, mexiletine, sulfisoxazole, and torasemide useful for enhancing memory and mental functions such as alertness, attention, reasoning, concentration, learning, or language processing, in a subject in need thereof.

BACKGROUND OF THE INVENTION

In a rapidly evolving society, with an always increasing exposure to saturating information and requirements in terms of mental performance, there is a growing demand of drugs able to sustain mental functions such as memory, cognition, intelligence, motivation, attention and concentration even for healthy people. Such drugs, named nootropics, smart drugs, memory enhancers, cognitive enhancers and intelligence enhancers consists in drugs, supplements, nutraceuticals, and functional food [1]. Main features of nootropics are the enhancement of learning and memory acquisitions as well as resistance of learned behaviors to agents that tend to impair them as well as protection of brain against various physical or chemical injuries and finally facilitation of interhemispheric flow of information and efficient tonic cortical/subcortical mechanism [2]. Absence of the usual negative pharmacologic effects of psychotropic drugs is also expected, since these agents are dedicated among others to healthy, both young and aging, patients. These drugs that improve performance on cognitive tasks in healthy individuals are typically developed to treat cognitive incapacities and improve the quality of life for patients suffering of neuropsychiatric disorders and brain injury [3].

Facing social pressure, more and more people are prompted to use drugs usually prescribed for treating disabling diseases in the sole aim of raising their working and efficiency potential, without regarding at the potential side effects or addiction provoked by a misuse of such drugs. The growing market demand for such drugs or supplements makes that several drugs or dietary supplements are available to the consumer, over the counter, without any positive effect on memory or related mental functions that has been formally scientifically demonstrated.

Precise mechanisms of action of nootropics are unknown. Extensive studies have revealed various pharmacological effects. It is supposed that they act by altering the availability of the brain's supply of neurochemicals such as neurotransmitters, enzymes, and hormones by improving the brain's oxygen supply, or by stimulating nerve growth.

Nootropics belong to many different categories, that are the following: traditional herbs, vitamins and supplements, recreational drugs, racetams, stimulants, dopaminergics, concentration and memory enhancement (cholinergics, GABA blockers, glutamate activators, phosphodiesterase inhibitors, Alpha-2A adrenergic receptor agonists), serotonergics, anti-depression, adaptogenic (antistress) and mood stabilization agents, vasodilators improving blood flow and metabolic function, histamine agonists (experimental), anti-oxidant and neuroprotectant drugs, hormones and secondary enhancers.

Piracetam that belongs to the racetam category was the first nootropic agent discovered and licensed in many countries for myoclonus, stroke and mild cognitive impairment. Piracetam is among the toxicologically safest drugs ever developed. As an example, it has been reported that a two week regimen of piracetam enhanced verbal memory in healthy college students [4]. It also displayed therapeutic benefit in schizophrenic patients when combined with typical neuroleptics [5]. Other drugs showed improvement in cognitive functions, such as d-cycloserine in anxiety disorders [6], levetiracetam in epilepsy [7,8] and alcohol withdrawal [9], and donepezil in mental retardation [10] amongst others. But most of these drugs are not devoid from detrimental side effects.

Baclofen, a GABAB receptor agonist, is known to induce anterograde amnesia in rodents [11]. More recently, recurrent spells of amnesia have been reported in a woman subjected to intrathecal instillation of baclofen in the frame of a treatment for dystonia [12]. Similarly, a clinical study about the effects of acamprosate on healthy young human subjects has shown that acamprosate impairs free recall, supporting the hypothesis that acamprosate impairs memory functions [13].

As shown herein, the inventors have found combinations of particular drugs that are efficient to stimulate cognition in vivo, particularly in healthy subjects, and which represent novel improved safe and efficient nootropic agents.

SUMMARY OF THE INVENTION

An object of the invention resides in a composition comprising a combination of at least two drugs selected from baclofen, acamprosate, cinacalcet, mexiletine, sulfisoxazole, and torasemide, or salt(s), prodrug(s), derivative(s), or sustained release formulation(s) thereof, for use as a stimulator of cognitive function in a subject in need thereof.

Another object of the invention resides in method for stimulating cognition in a subject in need thereof, comprising administering to the subject a combination of at least two drugs selected from baclofen, acamprosate, cinacalcet, mexiletine, sulfisoxazole, and torasemide, or salt(s), prodrug(s), derivative(s), or sustained release formulation(s) thereof.

In a preferred embodiment, the compositions for use in the invention comprise a combination of drugs selected from:
  baclofen and acamprosate,
  mexiletine and cinacalcet,
  baclofen and torasemide, or
  sulfisoxazole and torasemide.

The invention is particularly suited to stimulate (e.g., improve, enhance or increase) memory, learning, reasoning, alertness, attention, concentration, language processing, and/or the ability to cope with socio-professional burden in said subject.

The invention is particularly suitable for use in healthy subjects who have no known clinical signs of a disease (particularly subjects who do not suffer from vascular dementia, senile dementia, age-associated memory impairment, Alzheimer's disease, Lewy body dementia or mild cognitive impairment), and who only have a need for improved or stimulated cognitive capacities, either temporarily, or for longer periods of time.

The invention may also be used, either in a curative or preventive regimen, in subjects having, having had, or at risk of having particular disorders which affect cognition such as a psychiatric disorder, mental retardation, chemical induced memory disturbances or amnesia, a dietary or metabolism deficiency, a learning, language, calculating and/or reading disability, or drug withdrawal.

The invention may be used in any mammalian subject, preferably in human subjects.

DETAILED DESCRIPTION OF THE INVENTION

Figure 1:
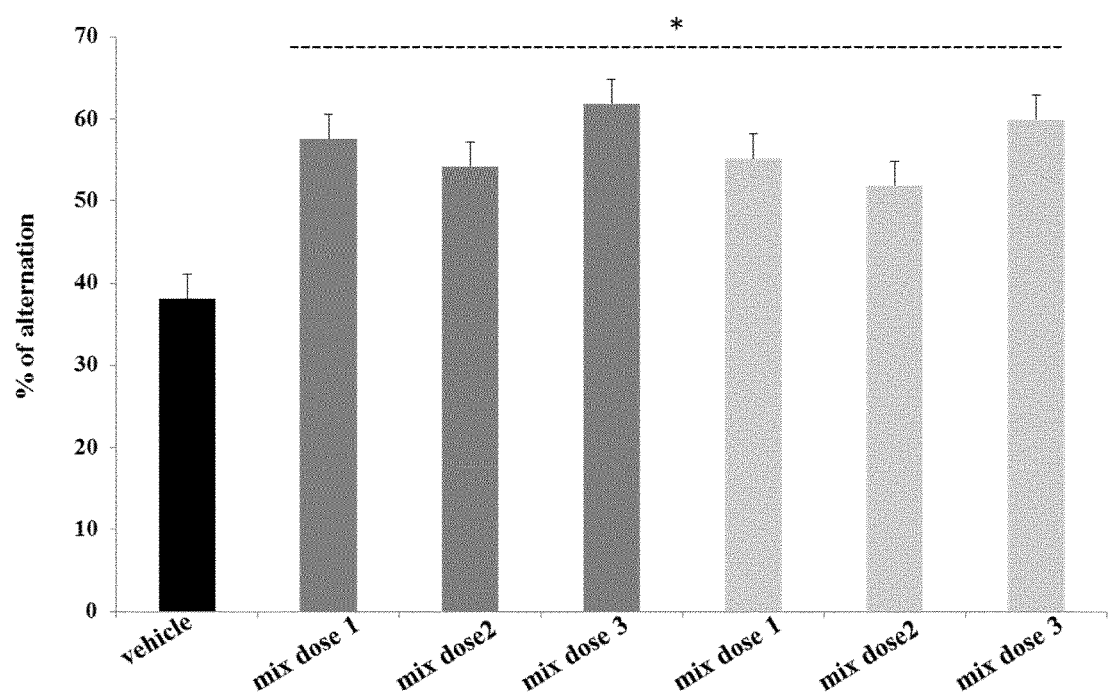
FIG. 1: Baclofen and acamprosate combinations are efficient in significantly improving learning and working memory performances (in T-maze alternation task) of mice whatever the concentrations tested (cf. table I) and regardless duration of treatment (from 7 days (dark grey bars) or 2 hours (light grey bars) before the test); black bar: vehicle dosed animals; *: significantly different from vehicle, ANOVA and Dunnett's test).

The present invention relates to compositions and methods for improving or stimulating memory and related mental functions in a subject. More particularly, the invention discloses the use of a composition comprising a combination of at least:
baclofen and acamprosate,
mexiletine and cinacalcet,
baclofen and torasemide, or
sulfisoxazole and torasemide,
as a nootropic efficient in improving memory and related mental functions in a mammal Memory (or more precisely learning and memory phenomenon) is a generic term for complex brain processes by which the various information perceived by the brain are stored, encoded and retrieved. Memory proceeds from the storage of all kind of information which are received by the organism: motor, language, visual, emotions, odors etc. Physiologically, these processes stem in an enhancement of the synaptic responses (through modulation of synaptic strength and synapse formation phenomenon called long term potentiation) and in neuron network densification through creation of neuronal connections. Scientists make a distinction between short-term (also called working memory) and long term memory. Short-term memory is a brief retention of information (lasting minutes to hours) and is limited in its capacity. Long term memory allows the storage of much more information and this, for an indefinite duration (as long as life-time). Long term memory has been found to be itself composed of different subtypes of memories which are often interrelated. The transition between the two types of memory is called memory consolidation, and is the result of the strengthening of the connections between the different brain areas and of the integration of the information coming from these different areas. Transition from short- to long-term memory usually occurs by the repetitive stimulation of neurons. Hippocampus has been shown to play a pivotal role in consolidation process: the alteration in the volume of hippocampus observed in alcoholics has been correlated with the cognitive and memory impairment which they often experience.

Loss of remembrance is usually attributed to an activity-dependent reduction in the strength of neuronal synapses that are less stimulated or active. An excess of new information, needing the strengthening of former synapses or the creation of new synapses, can also weaken other older ones thereby implying the forgetting of previously stored information. Conversely, incapacity to store further information can be due to the excess of older ones. Hence, environmental factors as high flow of data to store or to cope with may influence the memory and related mental functions.

Other factors like lack of sleep, stress, emotional states, psychiatric diseases, drug abuse, or drug intake are known to influence memory and related mental functions, notably by having an effect on the storage of information by weakening or strengthening synapses.

The inventors have surprisingly found that compositions comprising at least two drugs selected from baclofen, acamprosate, cinacalcet, mexiletine, sulfisoxazole, and torasemide combination are particularly effective, in vivo, for enhancing memory performances of different tasks implying short or long time memory as well as related mental functions.

Within the context of the invention the term "memory" encompasses short term and long term memory.

Within the context of this invention, the term "mental functions" includes cognitive tasks which are implicated or can sustain memory processes as concentration, alertness, attention, learning, reasoning, or language processing.

Though compositions of the invention can be used in the aim of improving memory and/or mental functions in any mammal, it should be contemplated that such improvement may be particularly desirable in healthy people having to face to high performance requirements, willing to improve, or maintain, their performances and their cognitive wellness. Such people being, for example, people punctually or chronically in need for a raising of their memory, learning, or alertness performances as students, caregivers, pilot line or, more generally, people having to face to mental fatigue, lack of sleep, mental daily stress, occupational stress, or having to deal with multi tasks activities. In other words, compositions of the invention are destined to people having to face with socio-professional burden. It can also concern other people with a memory complaint, for example, women experiencing memory loss during hormonal or imbalances changes as pregnancy, post-partum, in perimenaupose or menaupose. It is commonly accepted that even a small percentage increment in cognitive performance can lead to significant improvement in functional outcome (cf. "Brain science, addiction and drugs", report of the Academy of medical Sciences (UK), 2008). As those people are healthy people, they are not suffering from vascular dementia, senile dementia, age-associated memory impairment, Alzheimer's disease, Lewy body dementia, or mild cognitive impairment.

Other people in need for such stimulation or improvement are people experiencing, or at risk to experience, a condition which impairs their memory and/or memory related mental functions. Thus, the purpose of the present invention is not to treat the etiological cause of said memory impairing condition but to provide to people, experiencing or at risk to experience such a condition or disorder, an improvement of their wellness through improving their memory and/or memory related functions.

Such people being, for example:

People undergoing a treatment or exposed to toxics which have a negative effect on memory as substance abuse (as cocaine, heroin, cannabis, amphetamines . . . ), exposure to heavy metals (as lead, aluminum or mercury . . . ), medicines as barbiturates, benzodiazepines, anticholinergics (as scopolamine), anesthetics (as propofol), statins (as atorvastatin, rosuvastatin or simvastatin), or some antiseizure drugs (e.g. carbamazepine), first generation antihistaminergic drugs . . . Some of the drugs described as inducing memory loss are notably listed by Tannenbaum et al. [14].

People experiencing drug withdrawal.

People with a thyroid condition, resulting in hypothyroidism or hyperthyroidism, preferably hypothyroidism.

People suffering from disorders associated with mental retardation and selected from: Rubinstein-Taybi's syndrome, Greig's syndrome, Apert's syndrome, Angelman's syndrome, Coffin-Lowry's syndrome, Rett's syndrome, fragile X syndrome or William's syndrome.

People, particularly children, suffering from learning, language, calculating and/or reading pathological difficulties as, for example, dyscalculia, dysorthographia or dyslexia.

People suffering from psychiatric disorders as depression, psychotic disorders (as autism or schizophrenia), attention deficit hyperactivity disorders, anxiety or obsessional compulsive disorders.

People suffering from a dietary deficiency (resulting, from e.g. bariatric surgery, undernourishment or malnutrition, incomplete parenteral nutrition, diuretic therapy, drug intake) or from a chronic disease (e.g. infection, chronic diarrhea, celiac disease, Crohn's disease) responsible for metabolic deficiencies as iron deficiency, vitamin deficiencies like, for example, thiamine (vitamin B1) deficiency (e.g. Korsakoff's syndrome, Wernicke's encephalopathy), vitamin B6 deficiency, vitamin B12 deficiency, or inherited metabolism deficiencies (e.g. phenylketonuria which results in mental retardation).

As used herein, such people are not suffering from vascular dementia, senile dementia, age-associated memory impairment, Alzheimer's disease, Lewy body dementia, or mild cognitive impairment.

As used herein the term "improvement" means an increment in memory and/or related mental functions performance when compared to a previous measure or reference data. Such performance in memory and/or memory related mental functions can be measured using several memory and cognition tests well known in the art. It should be considered that said "improvement" can also be the maintenance of said performances compared to a former level, in a subject experiencing any of the above conditions or activities which could be, otherwise, expected to result in a weakening in performances of said memory and/or related mental functions.

As used herein, "treatment" of memory impairment in a subject suffering or having suffering from a cognitive disabling condition or disorder includes the therapy, prevention, prophylaxis, retardation or reduction of memory impairment and/or memory related mental functions deficits in a subject in need thereof as defined above.

Within the context of this invention, the designation of a specific drug or compound is meant to include not only the specifically named molecule, but also any pharmaceutically acceptable salt, hydrate, derivative, isomer, racemate, conjugate, prodrug or derivative thereof of any chemical purity.

The term "combination or combinatorial treating/therapy" designates a treatment wherein compound(s) and/or drugs are co-administered to a subject to cause a biological effect. In a combined therapy according to this invention, the at least two drugs may be administered together or separately, at the same time or sequentially. Also, compound(s) and/or drug(s) of the invention may be administered through different routes and protocols. As a result, although they may be formulated together, the drugs of a combination may also be formulated separately.

The term "prodrug" as used herein refers to any functional derivatives (or precursors) of a compound of the present invention, which, when administered to a biological system, generates said compound as a result of e.g., spontaneous chemical reaction(s), enzyme catalysed chemical reaction(s), and/or metabolic chemical reaction(s). Prodrugs typically have the structure X-drug wherein X is an inert carrier moiety and drug is the active compound. Usually, the prodrug devoid of activity or less active than the drug and the drug is released from the carrier in vivo. Prodrugs are usually inactive or less active than the resulting drug and can be used, for example, to improve the physicochemical properties of the drug, to target the drug to a specific tissue, to improve the pharmacokinetic and pharmacodynamic properties of the drug and/or to reduce undesirable side effects. Some of the common functional groups that are amenable to prodrug design include, but are not limited to, carboxylic, hydroxyl, amine, phosphate/phosphonate and carbonyl groups. Prodrugs typically produced via the modification of these groups include, but are not limited to, esters, carbonates, carbamates, amides and phosphates. Specific technical guidance for the selection of suitable prodrugs is general common knowledge [15-19]. Furthermore, the preparation of prodrugs may be performed by conventional methods known by those skilled in the art. Methods which can be used to synthesize other prodrugs are described in numerous reviews on the subject [15, 20-25]. For example, arbaclofen placarbil is listed in ChemID plus Advance database (website: chem.sis.nlm.nih.gov/chemidplus/) and arbaclofen placarbil is a well-known prodrug of baclofen [26, 27]).

The term "derivative" of a compound includes any molecule that is functionally and/or structurally related to said compound, such as an acid, amide, ester, ether, acetylated variant, hydroxylated variant, or an alkylated (C1-C6) variant of such a compound. The term derivative also includes structurally related compound having lost one or more substituent as listed above. For example, homotaurine is a deacetylated derivative of acamprosate. Preferred derivatives of a compound are molecules having a substantial degree of similarity to said compound, as determined by known methods. Similar compounds along with their index of similarity to a parent molecule can be found in numerous databases such as PubChem (http://pubchem.ncbi.nlm.nih.gov/search/) or DrugBank (http://www.drugbank.ca/). In a more preferred embodiment, derivatives should have a Tanimoto similarity index greater than 0.4, preferably greater than 0.5, more preferably greater than 0.6, even more preferably greater than 0.7 with a parent drug. The Tanimoto similarity index is widely used to measure the degree of structural similarity between two molecules. Tanimoto similarity index can be computed by software such as the Small Molecule Subgraph Detector [28, 29] available online (http://www.ebi.ac.uk/thornton-srv/software/SMSD/). Preferred derivatives should be both structurally and functionally related to a parent compound, i.e., they should also retain at least part of the activity of the parent drug.

The term derivatives also include metabolites of a drug, e.g., a molecule which results from the (biochemical) modification(s) or processing of said drug after administration to an organism, usually through specialized enzymatic systems, and which displays or retains a biological activity of the drug. Metabolites have been disclosed as being responsible for much of the therapeutic action of the parent drug. In a specific embodiment, a "metabolite" as used herein designates a modified or processed drug that retains at least part of the activity of the parent drug.

The term "salt" refers to a pharmaceutically acceptable and relatively non-toxic, inorganic or organic acid addition salt of a compound of the present invention. Pharmaceutical salt formation consists in pairing an acidic, basic or zwitterionic drug molecule with a counterion to create a salt version of the drug. A wide variety of chemical species can be used in neutralization reaction. Pharmaceutically acceptable salts of the invention thus include those obtained by reacting the main compound, functioning as a base, with an inorganic or organic acid to form a salt, for example, salts of acetic acid, nitric acid, tartric acid, hydrochloric acid, sulfuric acid, phosphoric acid, methane sulfonic acid, camphor sulfonic acid, oxalic acid, maleic acid, succinic acid or citric acid. Pharmaceutically acceptable salts of the invention also include those in which the main compound functions as an acid and is reacted with an appropriate base to form, e.g., sodium, potassium, calcium, magnesium, ammonium, or choline salts. Though most of salts of a given active principle are bioequivalents, some may have, among others, increased solubility or bioavailability properties. Salt selection is now a common standard operation in the process of drug development as teached by H. Stahl and C. G Wermuth in their handbook [30].

In a preferred embodiment, the designation of a compound is meant to designate the compound per se, as well as any pharmaceutically acceptable salt, hydrate, isomer, racemate, ester or ether thereof.

In a more preferred embodiment, the designation of a compound is meant to designate the compound as specifically designated per se, as well as any pharmaceutically acceptable salt thereof.

In a particular embodiment, a sustained-release formulation of the compound is used.

As discussed above, the invention relates to particular drug compositions which have a strong unexpected effect on memory and related mental functions involved in memory processes. These drug combinations therefore represent novel approaches for improving memory in subject in need thereof. More specifically, the invention discloses compositions, comprising at least two drugs selected from cinacalcet, baclofen, acamprosate, mexiletine, sulfisoxazole, and torasemide, which provide a significant and synergistic effect, in vivo, on memory and memory-related mental functions performances.

Indeed, as shown in the experimental part, combination therapies of the invention can substantially improve the learning and memory performances of subjects. In particular, the inventors have surprisingly discovered that combinations of the invention have a strong, unexpected positive effect on short and long term memory in either healthy subjects or subjects experiencing cognitive disabling conditions. They show, also, such an effect for drug induced amnesia. Though efficient alone, at doses found by the inventors, the examples also show that, combination therapies of the invention may be effective at very low doses for which drugs alone do not confer any improvement in learning and memory performances. These results are remarkable and particularly advantageous since, at such low doses, any possible side effects, if any, are likely to be avoided.

Illustrative CAS numbers for the above cited drugs are provided in table 1 below. Table 1 cites also, in a non-limitative way, common salts, racemates, prodrugs, metabolites or derivatives for these compounds used in the compositions of the invention.

TABLE 1

| Drug | CAS Numbers | Class or Tanimoto similarity index |
|---|---|---|
| Acamprosate and related compounds | | |
| Acamprosate | 77337-76-9; 77337-73-6 | NA |
| Homotaurine | 3687-18-1 | 0.73 |
| Ethyl dimethyl ammonio propane sulfonate | / | 0.77 |
| Taurine | 107-35-7 | 0.5 |
| Baclofen and related compounds | | |
| Baclofen | 1134-47-0; 66514-99-6; 69308-37-8; 70206-22-3; 63701-56-4; 63701-55-3 | NA |
| 3-(p-chlorophenyl)-4-hydroxybutyric acid | / | Metabolite |
| Arbaclofen placarbil | 847353-30-4 | Prodrug |
| Mexiletine and related compounds | | |
| Mexiletine | 31828-71-4; 5370-01-4 | |
| 6-Hydroxymethylmexiletine | 53566-98-6 | Metabolite |
| 4-Hydroxymexiletine | 53566-99-7 | Metabolite |
| 3-Hydroxymexiletine (MHM) | 129417-37-4 | Metabolite |
| N-Hydroxymexiletine glucuronide | 151636-18-9 | Metabolite |
| Sulfisoxazole and related compounds | | |
| Sulfisoxazole | 127-69-5; 4299-60-9 | |
| N(4)-Acetylsulfisoxazole | 4206-74-0 | Metabolite |
| Sulfisoxazole acetyl | 80-74-0 | Prodrug |
| Sulfamethoxazole | 723-46-6 | 0.52 |
| Cinacalcet and related compounds | | |
| Cinacalcet | 226256-56-0; 364782-34-3 | |
| Hydrocinnamic acid | 501-52-0 | Metabolite |
| Torasemide and related compounds | | |
| Torasemide | 56211-40-6; 72810-59-4 | |
| Hydroxytorasemide | 99300-68-2; 99300-67-1 | Metabolites |
| Carboxytorasemide | | Metabolite |
| Tolbutamide | 64-77-7 | 0.55 |

Specific examples for baclofen prodrugs are given in Hanafi et al. [31] who had shown baclofen esters and ester carbamates as of particular interest for CNS targeting. Hence such prodrugs are particularly suitable for compositions of this invention. Arbaclofen placarbil as mentioned before is also a well-known prodrug and may thus be used instead of baclofen in compositions of the invention. Other prodrugs for baclofen can be found in the following patent applications: WO2010102071, US2009197958, WO2009096985, WO2009061934, WO2008086492, US2009216037, WO2005066122, US2011021571, WO2003077902, WO2010120370.

Useful prodrugs for acamprosate such as pantoic acid ester neopentyl sulfonyl esters, neopentyl sulfonyl esters prodrugs or masked carboxylate neopentyl sulfonyl ester prodrugs of acamprosate are notably listed in WO2009033069, WO2009033061, WO2009033054 WO2009052191, WO2009033079, US 2009/0099253, US 2009/0069419, US 2009/0082464, US 2009/0082440, and US 2009/0076147.

In an embodiment the invention relates to the use of at least two drugs selected from cinacalcet, baclofen, acamprosate, mexiletine, sulfisoxazole, and torasemide for the manufacture of a medicament for improving the memory and/or memory related mental functions in a subject in need thereof.

In a particular embodiment the invention relates to a composition comprising at least two drugs selected from cinacalcet, baclofen, acamprosate, mexiletine, sulfisoxazole, and torasemide for use for improving memory and related mental functions in a subject in need thereof.

In another embodiment the invention relates to a method for improving memory and/or mental related functions in a subject in need thereof, such method comprising administering at least two drugs selected from cinacalcet, baclofen, acamprosate, mexiletine, sulfisoxazole, and torasemide to said subject.

In a preferred embodiment the invention relates to a the use of a composition comprising at least two drugs selected from cinacalcet, baclofen, acamprosate, mexiletine, sulfisoxazole, and torasemide for increasing memory, learning, attention, reasoning, concentration, language processing or alertness performances in a subject in need thereof.

In another preferred embodiment the invention relates to the use of a composition comprising at least two drugs selected from cinacalcet, baclofen, acamprosate, mexiletine, sulfisoxazole, and torasemide for improving short term and/or long term memory in a subject in need thereof.

In a another embodiment the invention relates to a composition comprising at least two drugs selected from cinacalcet, baclofen, acamprosate, mexiletine, sulfisoxazole, and torasemide for use for improving memory and mental functions in a subject suffering, having suffered or at risk to suffer from a cognitive disabling condition or disorder as defined above.

In a particular embodiment, the invention relates to the use of a composition comprising at least one drug combination selected from:
baclofen and acamprosate,
mexiletine and cinacalcet,
baclofen and torasemide, or
sulfisoxazole and torasemide,
for improving memory and mental functions in a subject in need thereof.

In a particular embodiment, the invention relates to the use of a composition comprising at least one drug combination selected from:
baclofen and acamprosate,
mexiletine and cinacalcet,
baclofen and torasemide, or
sulfisoxazole and torasemide,
for improving short term and/or long term memory in a subject in need thereof.

In a further embodiment, the invention relates to the use of a composition comprising at least one drug combination selected from:
  baclofen and acamprosate,
  mexiletine and cinacalcet,
  baclofen and torasemide, or
  sulfisoxazole and torasemide,
for increasing memory, learning, attention, reasoning, concentration, language processing or alertness performances in a subject in need thereof.

In another embodiment, the invention relates to the use of a composition comprising at least one drug combination selected from:
  baclofen and acamprosate,
  mexiletine and cinacalcet,
  baclofen and torasemide, or
  sulfisoxazole and torasemide,
for use in the prophylaxis or the treatment of memory and/or mental functions impairment in a subject suffering from a thyroid condition, resulting in hypothyroidism or hyperthyroidism.

In another embodiment, the invention relates to a composition comprising at least one drug combination for selected from:
  baclofen and acamprosate,
  mexiletine and cinacalcet,
  baclofen and torasemide, or
  sulfisoxazole and torasemide,
for use for the prophylaxis or the treatment of memory and/or mental functions impairment in a subject suffering, having suffered or at risk to suffer from a psychiatric disorder selected from depression, psychotic disorders (as autism or schizophrenia), attention deficit hyperactivity disorders, anxiety, or obsessional compulsive disorders.

In another embodiment, the invention relates to a composition comprising at least one drug combination for selected from:
  baclofen and acamprosate,
  mexiletine and cinacalcet,
  baclofen and torasemide, or
  sulfisoxazole and torasemide,
for use for the prophylaxis or the treatment of memory and/or mental functions impairment in a subject suffering from disorders associated with mental retardation and selected from: Rubinstein-Taybi's syndrome, Greig's syndrome, Apert's syndrome, Angelman's syndrome, Coffin-Lowry's syndrome, Rett's syndrome, fragile X syndrome or William's syndrome.

In another embodiment, the invention relates to a composition comprising at least one drug combination for selected from:
  baclofen and acamprosate,
  mexiletine and cinacalcet,
  baclofen and torasemide, or
  sulfisoxazole and torasemide,
for use for the prophylaxis or the treatment of memory and/or mental functions impairment in a subject suffering from a dietary or metabolic deficiency, undergoing a treatment or exposed to toxics.

The inventions also relates to a composition comprising at least one drug combination for selected from:
  baclofen and acamprosate,
  mexiletine and cinacalcet,
  baclofen and torasemide, or
  sulfisoxazole and torasemide,
for use for the prophylaxis or the treatment of memory and/or mental functions impairment in a subject suffering from learning, language, calculating and/or reading pathological difficulties as, for example, dyscalculia, dysorthographia or dyslexia.

The above compositions may be used alone or may be further combined with additional compounds. In this regard, in a particular embodiment, the compositions of the invention may further comprise at least one compound selected from, methimazole, prilocaine, dyphylline, quinacrine, carbenoxolone, aminocaproic acid, cabergoline, diethylcarbamazine, cinacalcet, cinnarizine, eplerenone, fenoldopam, leflunomide, levosimendan, sulodexide, terbinafine, zonisamide, etomidate, phenformin, trimetazidine, mexiletine, ifenprodil, moxifloxacin, bromocriptine or torasemide. Illustrative CAS numbers for each of these compounds are provided, in a non-limitative way, in table 2 below:

TABLE 2

| DRUG NAME | CAS NUMBER |
| --- | --- |
| Aminocaproic Acid | 60-32-2 |
| Bromocriptine | 25614-03-3 |
| Cabergoline | 81409-90-7 |
| Carbenoxolone | 5697-56-3 |
| Cinnarizine | 298-57-7 |
| Diethylcarbamazine | 90-89-1 |
| Dyphylline | 479-18-5 |
| Eplerenone | 107724-20-9 |
| Etomidate | 33125-97-2 |
| Fenoldopam | 67227-57-0 |
| Ifenprodil | 23210-56-2 or 23210-58-4 |
| Leflunomide | 75706-12-6 |
| Levosimendan | 141505-33-1 |
| Methimazole | 60-56-0 |
| Moxifloxacin | 354812-41-2 |
| Phenfonnin | 114-86-3 |
| Prilocaine | 721-50-6 or 14289-31-7 or 14289-32-8 |
| Quinacrine | 83-89-6 |
| Sulodexide | 57821-29-1 |
| Terbinafine | 91161-71-6 |
| Trimetazidine | 5011-34-7 or 13171-25-0 |
| Zonisamide | 68291-97-4 |

Hence, compositions of the invention can comprise 2, 3, 4, 5 or more active compounds which can be administered to the subject concomitantly, in a single dosage form, separately, or sequentially, in order to confer the more substantial effect. As shown in the experimental section, an improvement in memory and related mental functions is noticed even within the first hours after injection of compositions of the invention.

The above compositions can be also further combined with additional compounds, known or suspected to have any beneficial effect on memory and/or memory related mental functions of a subject. These additional compounds can be improved vegetal extracts (e.g. *Gingko biloba* extracts), natural compounds (as vitamins, fatty acids, isoflavones), a drug initially developed for treating a cognitive disorder as a racetam (e.g. levetiracetam, piracetam, pramiracetam, aniracetam, or oxiracetam) or an acetylcholine esterase inhibitor (e.g. donepezil, rivastigmine, galantamine).

Compositions of the invention can therefore comprise 1, 2, 3, 4, 5 or more additive ingredients, extracts or drugs, known or suspected to have any beneficial effect on memory performances. As stated previously, the compounds of the compositions can be administered to the subject concomitantly, in a single dosage form, separately, or sequentially in order to confer the more substantial effects.

More preferably one said additional compound is a racetam selected from levetiracetam, piracetam, pramiracetam, aniracetam, or oxiracetam. Even more preferably the racetam is selected from levetiracetam or piracetam.

In that view, one preferred embodiment of the invention is a combination comprising at least two drugs selected from baclofen, acamprosate, cinacalcet, mexiletine, sulfisoxazole, or torasemide in combination with at least levetiracetam or piracetam for use for improving memory and mental functions in a subject in need thereof.

A preferred embodiment of the invention more particularly relates to a composition comprising baclofen and acamprosate, in combination with at least one compound selected from levetiracetam or piracetam.

Another particularly preferred embodiment, said additional compound is an acetylcholinesterase inhibitor, selected from donepezil, rivastigmine or galantamine. Within the acetylcholinesterase inhibitors, donepezil is particularly preferred.

Consequently, in a preferred embodiment, the invention relates to a composition comprising at least two compounds selected from baclofen, acamprosate, cinacalcet, mexiletine, sulfisoxazole, or torasemide in combination with donepezil for use for the prophylaxis or the treatment of memory and/or mental functions impairment in a subject in need thereof.

Illustrative CAS numbers for each of these compounds are provided, in a non-limitative way, in table 3, below:

TABLE 3

| DRUG NAME | CAS NUMBER |
| --- | --- |
| Donepezil | 120014-06-4; 142057-79-2; 120011-70-3; 142057-77-0 |
| Rivastigmine | 123441-03-2; 129101-54-8 |
| Galatamine | 357-70-0; 1953-04-4 |
| Levetiracetam | 102767-28-2 |
| Piracetam | 7491-74-9 |
| Pramiracetam | 68497-62-1; 72869-16-0 |
| Aniracetam | 72432-10-1 |
| Oxiracetam | 62613-82-5 |

Memory rehabilitation training sessions are intensive memory and/or cognitive training exercises which aim to counter a short term memory deficit or to reorganize memory processes using intact brain areas to compensate injured ones. Such treatments are particularly used for improving memory and memory related mental functions of subject having experienced brain injury or brain surgery. In that view, compositions of the invention are particularly suitable in the aim of stabilizing and reinforcing synaptic processes triggered during these exercises. Hence, in a particular embodiment, the invention thus relates to the use of compositions of the invention to enhance efficacy of said memory rehabilitation training sessions. In a more particular embodiment, the compositions of the invention are administered just before a said training session, or, chronically, all along the rehabilitation period.

In the particular embodiment of preventing potential deleterious effect of toxics or drugs on the memory performances, the administration of the compositions of the invention to the subject is performed at least 2 hours, preferably 24 hours, before the exposure to said toxic(s) or drug(s). In another embodiment, administration of the compositions of the invention lasts all along exposure to said toxic(s) or drug(s), at regular intervals in order to maintain an effective level of the active compounds of said composition in the subject.

As a function of the needs of the subject undergoing the treatment of the invention, said treatment may be provided at home, the doctor's office, a clinic, a hospital's outpatient department, or a hospital, so that the doctor can observe the therapy's effects closely and make any adjustments that are needed.

The duration of the treatment depends also on the needs of the subject, age and condition of the subject, and how the subject responds to the treatment. The dosage, frequency and mode of administration of each component of the combination can be controlled independently. For example, one drug may be administered orally while the second drug may be administered intramuscularly. Combination therapy may be given in on-and-off cycles that include rest periods so that the patient's body has a chance to recovery from any as yet unforeseen side-effects. The drugs may also be formulated together such that one administration delivers all drugs.

The administration of each drug of the combination may be by any suitable means that results in a concentration of the drug that, combined with the other component, is able to ameliorate memory and related mental function performances of the subject.

While it is possible for the drugs the combination to be administered as the pure chemical it is preferable to present them as a pharmaceutical composition, also referred to in this context as pharmaceutical formulation. Possible compositions include those suitable for oral, rectal, topical (including transdermal, buccal and sublingual), or parenteral (including subcutaneous, intramuscular, intravenous and intradermal) administration.

More commonly these pharmaceutical formulations are prescribed to the subject in "patient packs" containing a number dosing units or other means for administration of metered unit doses for use during a distinct treatment period in a single package, usually a blister pack. "Patient packs" have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions. Thus, the invention further includes a pharmaceutical formulation, as herein before described, in combination with packaging material suitable for said formulations. In such a patient pack the intended use of a formulation for the combination treatment can be inferred by instructions, facilities, provisions, adaptations and/or other means to help using the formulation most suitably for the treatment. Such measures make a patient pack specifically suitable for and adapted for use for treatment with the combination of the present invention.

The drug may be contained, in any appropriate amount, in any suitable carrier substance. The drug may be present in an amount of up to 99% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols.

The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active drug substantially immediately upon administration or at any predetermined time or time period after administration.

The controlled release formulations include (i) formulations that create a substantially constant concentration of the drug within the body over an extended period of time; (ii) formulations that after a predetermined lag time create a substantially constant concentration of the drug within the body over an extended period of time; (iii) formulations that sustain drug action during a predetermined time period by maintaining a relatively, constant, effective drug level in the body with concomitant minimization of undesirable side effects associated with fluctuations in the plasma level of the active drug substance; (iv) formulations that localize drug action by, e.g., spatial placement of a controlled release composition adjacent to or in the diseased tissue or organ; and (v) formulations that target drug action by using carriers or chemical derivatives to deliver the drug to a particular target cell type.

Administration of drugs in the form of a controlled release formulation is especially preferred in cases in which the drug has (i) a narrow therapeutic index (i.e., the difference between the plasma concentration leading to harmful side effects or toxic reactions and the plasma concentration leading to a therapeutic effect is small; in general, the therapeutic index, TI, is defined as the ratio of median lethal dose (LD50) to median effective dose (ED50)); (ii) a narrow absorption window in the gastro-intestinal tract; or (iii) a very short biological half-life so that frequent dosing during a day is required in order to sustain the plasma level at a therapeutic level.

Any of a number of strategies can be pursued in order to obtain controlled release in which the rate of release outweighs the rate of metabolism of the drug in question. Controlled release may be obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner (single or multiple unit tablet or capsule compositions, oil solutions, suspensions, emulsions, microcapsules, microspheres, nanoparticles, patches, and liposomes).

Solid Dosage Forms for Oral Use

Formulations for oral use include tablets containing the composition of the invention in a mixture with non-toxic pharmaceutically acceptable excipients. These excipients may be, for example, inert diluents or fillers (e.g., sucrose, microcrystalline cellulose, starches including potato starch, calcium carbonate, sodium chloride, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., acacia, alginic acid, sodium alginate, gelatin, starch, pregelatinized starch, microcrystalline cellulose, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., stearic acid, silicas, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). A time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology.

Drugs may be mixed together in the tablet, or may be partitioned. For example, a first drug is contained on the inside of the tablet, and a second drug is on the outside, such that a substantial portion of the second drug is released prior to the release of the first drug.

Formulations for oral use may also be presented as chewable tablets, or as hard gelatin capsules wherein the active ingredient is mixed with an inert solid diluent (e.g., potato starch, microcrystalline cellulose, calcium carbonate, calcium phosphate or kaolin), or as soft gelatin capsules wherein the active ingredient is mixed with water or an oil medium, for example, liquid paraffin, or olive oil. Powders and granulates may be prepared using the ingredients mentioned above under tablets and capsules in a conventional manner.

Controlled release compositions for oral use may, e.g., be constructed to release the active drug by controlling the dissolution and/or the diffusion of the active drug substance.

Dissolution or diffusion controlled release can be achieved by appropriate coating of a tablet, capsule, pellet, or granulate formulation of drugs, or by incorporating the drug into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated metylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the drugs of the claimed combinations may also be in the form of a buoyant tablet or capsule (i.e., a tablet or capsule that, upon oral administration, floats on top of the gastric content for a certain period of time). A buoyant tablet formulation of the drug(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel bather around its surface. This gel bather takes part in maintaining a density of less than one, thereby allowing the tablet to remain buoyant in the gastric juice.

Liquids for Oral Administration

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable suspending agents are, for example, sodium carboxymethylcellulose, methylcellulose, sodium alginate, and the like.

Parenteral Compositions

Though oral administration is particularly preferred, the pharmaceutical composition may also be administered parenterally in respect to the health condition of the patient. Injection, infusion or implantation (intravenous, intramuscular, subcutaneous, or the like) in dosage forms, formulations, or via suitable delivery devices or implants containing conventional, non-toxic pharmaceutically acceptable carriers and adjuvants are possible. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. The composition may include suspending, solubilizing, stabilizing, pH-adjusting agents, and/or dispersing agents.

The pharmaceutical compositions according to the invention may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the drugs is only sparingly or slightly soluble in water, a dissolution enhancing or solubilizing agent can be added, or the solvent may include 10-60% w/w of propylene glycol or the like.

Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutamnine). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(glycolic acid) or poly(ortho esters)).

Alternative Routes

Although less preferred and less convenient, other administration routes, and therefore other formulations, may be contemplated. They could be used for example, in cases where oral administration of compound is difficult in respect with global health condition of the subject. In this regard, for rectal application, suitable dosage forms for a composition include suppositories (emulsion or suspension type), and rectal gelatin capsules (solutions or suspensions). In a typical suppository formulation, the active drug(s) are combined with an appropriate pharmaceutically acceptable suppository base such as cocoa butter, esterified fatty acids, glycerinated gelatin, and various water-soluble or dispersible bases like polyethylene glycols. Various additives, enhancers, or surfactants may be incorporated.

The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

The preservatives, humectants, penetration enhancers may be parabens, such as methyl or propyl p-hydroxybenzoate, and benzalkonium chloride, glycerin, propylene glycol, urea, etc.

The pharmaceutical compositions described above for topical administration on the skin may also be used in connection with topical administration onto or close to the part of the body that is to be treated. The compositions may be adapted for direct application or for application by means of special drug delivery devices such as dressings or alternatively plasters, pads, sponges, strips, or other forms of suitable flexible material.

Dosages and Duration of the Treatment

It will be appreciated that the drugs of the combination may be administered concomitantly, either in the same or different pharmaceutical formulation or sequentially. If there is sequential administration, the delay in administering the second (or additional) active ingredient should not be such as to lose the benefit of the efficacious effect of the combination of the active ingredients. A minimum requirement for a combination according to this description is that the combination should be intended for combined use with the benefit of the efficacious effect of the combination of the active ingredients. The intended use of a combination can be inferred by facilities, provisions, adaptations and/or other means to help using the combination according to the invention.

Therapeutically effective amounts of the drugs in a combination of this invention include, e.g., amounts that are effective for enhancing learning and memory performances or preventing or reducing the diminution of these performances.

Although the active drugs of the present invention may be administered in divided doses, for example two or three times daily, a single daily dose of each drug in the combination is preferred, with a single daily dose of all drugs in a single pharmaceutical composition (unit dosage form) being most preferred.

Administration can be one to several times daily for several days to several years, and may even be for the life of the patient. Chronic or at least periodically repeated administration is indicated in most cases.

The term "unit dosage form" refers to physically discrete units (such as capsules, tablets, or loaded syringe cylinders) suitable as unitary dosages for human subjects, each unit containing a predetermined quantity of active material or materials calculated to produce the desired therapeutic effect, in association with the required pharmaceutical carrier.

The amount of each drug in a preferred unit dosage composition depends upon several factors including the administration method, the body weight and the age of the patient, the need of the subject, the risk of potential side effects considering the general health status of said subject. Additionally, pharmacogenomic (the effect of genotype on the pharmacokinetic, pharmacodynamic or efficacy profile of a therapeutic) information about a particular subject may affect the dosage used.

Except when responding to especially situations, where higher dosages may be required, the preferred dosage of each drug in the combination will usually lie within the range of doses not above the dosage usually prescribed for long-term maintenance treatment or proven to be safe in phase 3 clinical studies.

One remarkable advantage of the invention is that each compound may be used at low doses in a combination therapy, while producing, in combination, a substantial clinical benefit to the subject. The combination therapy may indeed be effective at doses where the compounds have individually low or no effect. Accordingly, a particular advantage of the invention lies in the ability to use sub-optimal doses of each compound, i.e., doses which are lower than therapeutic doses usually prescribed, preferably ½ of therapeutic doses, more preferably ⅓, ¼, ⅕, or even more preferably 1/10 of therapeutic doses. In particular examples, doses as low as 1/20, 1/30, 1/50, 1/100, or even lower, of therapeutic doses are used.

At such sub-therapeutic dosages, the compounds would exhibit no side effect, while the combination(s) according to the invention are fully effective in improving memory and related mental functions as defined above.

A preferred dosage corresponds to amounts from 1% up to 50% of those usually prescribed for long-term maintenance treatment.

The most preferred dosage may correspond to amounts from 0.1% up to 10% of those usually prescribed for long-term maintenance treatment.

Specific examples of dosages of drugs (referring to the actual active moiety, regardless of the salt which is used) for use in the invention are provided below:

Acamprosate between 0.1 and 500 mg/day, preferably less than 250 mg per day, more preferably less than 100 mg/day, even more preferably less than 10 mg/day, such dosages being particularly suitable for oral administration.

Baclofen between 0.01 to 200 mg per day, preferably less than 150 mg per day, more preferably less than 70 mg/day, even more preferably less than 35 mg/day, such dosages being particularly suitable for oral administration.

Mexiletine orally from about 6 to 120 mg per day, preferably less than 60 mg per day, more preferably less than 30 mg per day, such dosages being particularly suitable for oral administration, Torasemide orally from about 0.05 to 4 mg per day, preferably less than 2 mg per day, more preferably less than 1 mg per day, such dosages being particularly suitable for oral administration, Sulfisoxazole orally from about 20 to 800 mg per day, preferably less than 400 mg per day, more preferably less than 200 mg per day, such dosages being particularly suitable for oral administration, Cinacalcet orally from about 0.3 to 36 mg per day, preferably less than 20 mg per day, more preferably less than 10 mg per day, such dosages being particularly suitable for oral administration.

Aminocaproic acid orally from about 0.1 g to 2.4 g per day,

Bromocriptine orally from about 0.01 to 10 mg per day,

Diethylcarbamazine orally from about 0.6 to 600 mg per day,

Cabergoline orally from about 1 to 10 µg per day,

Cinnarizine orally from about 0.6 to 23 mg per day,

Dyphylline orally from about 9 to 320 mg per day,

Eplerenone orally from about 0.25 to 10 mg per day,

Ifenprodil orally from about 0.4 to 6 mg per day,

Leflunomide orally from about 0.1 to 10 mg per day,

Levosimendan orally from about 0.04 to 0.8 mg per day,

Moxifloxacin orally from about 4 to 40 mg per day,

Phenformin orally from about 0.25 to 15 mg per day,

Quinacrine orally from about 1 to 30 mg per day,

Sulodexide orally from about 0.05 to 40 mg per day,

Terbinafine orally from about 2.5 to 25 mg per day,

Trimetazidine orally from about 0.4 to 6 mg per day,

Zonisamide orally from about 0.5 to 50 mg per day.

When the composition comprises, as active ingredients, only baclofen and acamprosate, these two compounds may be used in different ratios, e.g., at a weight ratio acamprosate calcium/baclofen comprised between from 0.05 to 1000 (w/w), preferably between 0.05 to 100 (w/w), more preferably between 0.05 to 50 (w/w). In a preferred embodiment, the acamprosate calcium/baclofen ratio is 1/15. In another embodiment the acamprosate calcium/baclofen ratio is 4/3 or even 8/3.

In an embodiment, 1 mg of acamprosate calcium is given as a daily dose. In another embodiment, 40 mg of acamprosate is given as a daily dose. In still another embodiment such a daily dose is 80 mg.

It will be understood that the amount of the drug actually administered will be determined by a physician, in the light of the relevant circumstances including the condition or conditions to be treated, the exact composition to be administered, the age, weight, and response of the individual patient, the severity of the patient's symptoms, and the chosen route of administration. Therefore, the above dosage ranges are intended to provide general guidance and support for the teachings herein, but are not intended to limit the scope of the invention.

The following examples are given for purposes of illustration and not by way of limitation.

EXAMPLES

All animal procedures have been conducted in compliance to the existing legislation and regulations (Decree No.

87-848 of 19 Oct. 1987: implemented in April 1988, incorporated Directive 86/609/EC into French law, amended by Decree No. 2001-464 of 29 May 2001 and by Decision of 20 Jun. 2001).

I. Memory Improvement in Animals.

Short term and long term memory is assessed in healthy animals using different tests commonly used for learning and memory performances measurement.

A. Short Term and Long Term Memory Enhancement in Healthy Animals.

11 month-old C57B1/6 mice are used. They are group-housed (5-10 mice per cage) and maintained in a room with controlled temperature (21-22° C.) and a reversed light-dark cycle (12 h/12 h; lights on: 17:30-05:30; lights off: 05:30-17:30) with food and water available ad libitum.

1) Administration of Compounds

Drugs are solubilized in water and freshly prepared just before each gavage or ip administration and are kept under agitation.

Doses of drugs of the invention are exemplified in table 4. Concerning acamprosate calcium, the indicated doses refer to the doses of the salt of molecule.

TABLE 4

| mix doses used in mice | (+/−)Baclofen (mg/kg) | Acamprosate calcium (mg/kg) |
| --- | --- | --- |
| mix dose 1 | 1.2 | 0.08 |
| mix dose 2 | 3 | 0.2 |
| mix dose 3 | 7.5 | 0.5 |
| mix dose 4 | 0.48 | 0.032 |
| mix dose 5 | 0.192 | 0.0128 |

Donepezil, an acetylcholinesterase inhibitor, was used as an internal positive control. It is usually administered once, by ip, 30 min before the memory test.

Chronic Administration of Compounds, 7 Days Long Before the Test.

Between day 0 and day 7, drug combinations or the vehicle solution were administered twice daily (at 8:00 am and 6:00 pm). One animal group receives donepezil (reference compound 0.3 mg/kg) at 8:00 am and the vehicle at 6:00 pm.

On day 8, all animals were tested for the % of alternation performance in the T-maze test, 2 hours after the administration of drugs combination or the vehicle solution.

Administration of Compounds 1 Day Before the Test.

The eve of the test, drug combinations or the vehicle solution were administered at 8:00 am and 6:00 pm. One animal group received donepezil (reference compound 0.3 mg/kg) at 8:00 am and the vehicle at 6:00 pm. The day of the test, animals were administered with the drug combinations or vehicle 2 hours prior to perform the test.

Acute Administration of Compounds: Once, 2 Hours Before the Test.

The day of the test animals were administered with one dose of the drug combinations, the drugs alone, or vehicle, 2 hours prior to perform the test.

2) Improvement of Short Term Memory:

% of Alternation in T MAZE Test

Spontaneous alternation is the innate tendency of rodents to alternate free choices in a T-maze over a series of successive runs [32]. This sequential procedure relies on short-term memory.

The effect of the administration of combinations on short term memory was assessed for different durations of treatment (7 days, 1 day, 2 hours before the test).

The experiment was performed between 8:00 am and 3:00 pm under red light condition since the mice are held on a reversed light cycle. During the trials, animal handling and the visibility of the operator has been minimized as much as possible.

The T-maze apparatus is made of grey Plexiglas with a main stem (55 cm long×10 cm wide×20 cm high) and two arms (30 cm long×10 cm wide×20 cm high) positioned at 90 degree angle relative to the main stem. A start box (15 cm long×10 cm wide) is separated from the main stem by a sliding door. Sliding doors are also provided to close specific arms during the force choice alternation task [33].

The experimental protocol consists of one single session, which starts with 1 "forced-choice" trial, followed by 14 "free-choice" trials. In the first "forced-choice" trial, the animal is confined 5 s in the start arm and then it is released while either the left or right goal arm is blocked by closing the sliding door. Then the animal explores the open arm and returns to the start arm. At this point, the animal has completed the forced-choice trial. Immediately after the return of the animal to the start position, the left or right goal door is opened and the animal is allowed to freely choose between the left and right goal arm ("free choice" trials). Each time that the animal has chosen a goal arm, the opposite arm is closed in order to oblige the animal to return to the start arm. Once the animal returns to the start arm, all goal doors are opened to allow another round of free choice trial to begin. The animal is considered as entered in a choice arm when it places its four paws in the arm. A session is terminated and the animal is removed from the maze as soon as 14 free-choice trials have been performed or 15 min have elapsed, whatever event occurs first.

The apparatus was cleaned between each animal using alcohol (70°). Urine and feces were removed from the maze.

Results

The percent spontaneous alternation was calculated as the number of spontaneous alternations divided by the number of free-choice trials. An alternation is defined as a succession of 2 different arms over consecutive choices (e.g., the sequence right-left-right represents 2 alternations).

Analysis of variance (ANOVA) has been performed on the result data. Dunnett's or student's tests were applied to determine significance of differences.

Combinations of the invention are efficient in improving spontaneous alternation in dosed animals (table 5).

TABLE 5

| Animals dosed with: | Improvement in spontaneous alternation |
| --- | --- |
| Baclofen and acamprosate | + |
| Baclofen and torasemide | + |
| Mexiletine and cinaclacet | + |
| Sulfisoxazole and torasemide | + |
| Vehicle | − |

+: improvement;
−: no improvement.

FIG. 1 clearly shows that combinations of the invention are efficient in enhancing memory performances of the animals, at any of the tested doses (cf. table 4) of the baclofen and acamprosate combination. A significant enhancement in learning and memory performance up to 62% is observed for the chronic treatment and 57% for the mice submitted to the acute treatment.

Figure 2:
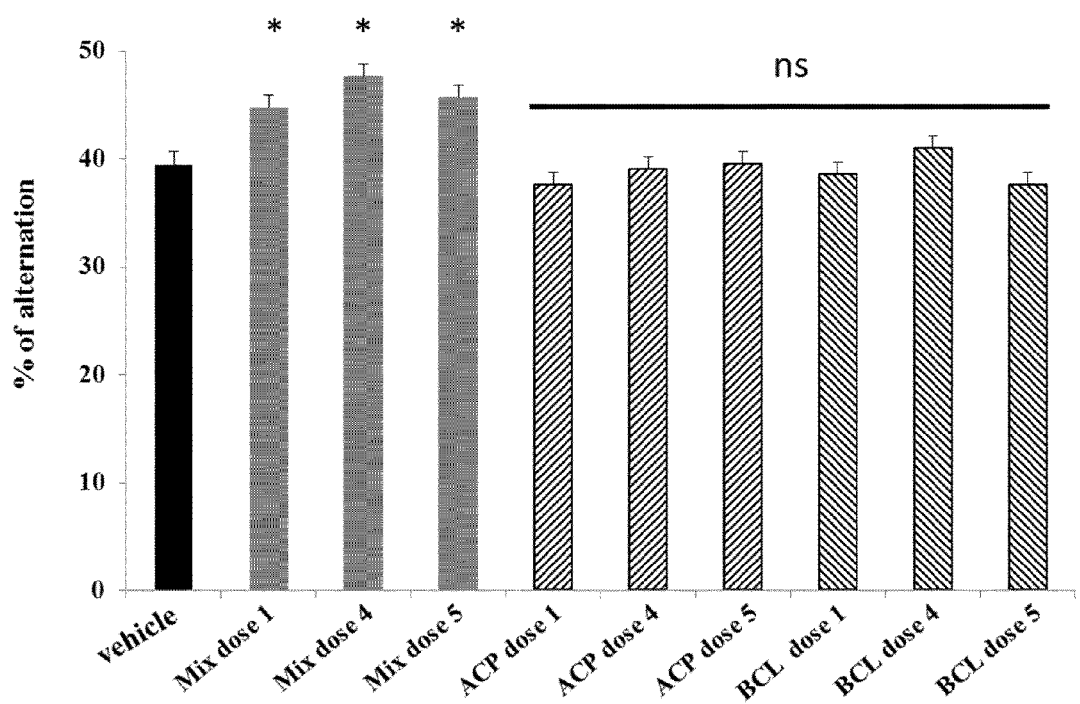
FIG. 2: Baclofen and acamprosate, when combined and administered once only 2 hours before the test, act synergistically for improving learning and working memory performances (in T-maze alternation task). A significant positive effect of baclofen (BCL) and acamprosate (ACP) combinations is observed for very low doses (dark grey bars) whereas, at such concentrations, no significant improvement is observed for any one of the molecule when used alone (dashed bars). (*: significantly different from vehicle dosed animals (black bar), Student's T-test; ns: not significantly different from vehicle). Black bar: vehicle dosed animals.

Moreover, compositions comprising baclofen and acamprosate are efficient in improving learning and memory performances of mice at very low doses of mix doses 4 and 5, as shown in FIG. 2.

It is noteworthy that combinations of the invention act very quickly as an improvement in memory performance is noticed even when drugs are administrated once, 2 hours before the test, and at concentrations as low as dose 5 (0.0128 mg/kg for acamprosate calcium and 0.192 mg/kg for baclofen, FIG. 2).

Surprisingly, an important synergistic effect between drugs, even at very low doses is observed (FIG. 2) whereas at these doses, the drugs, when administered alone, do not exhibit any significant positive effect on animal performances.

Delay Matching to Place in the Water Maze (Spatial Working Memory):

The same scheme of drug administration is applied. All animals are tested for learning and spatial short term memory.

The water-maze is a circular pool (diameter 140 cm, height 40 cm). The water temperature, 23±1° C., light intensity, external cues in the room (sink, contrasted posters, shelves), and water opacity are rigorously reproduced for each assay. A transparent Plexiglas non-slippery platform (diameter 10 cm) is immersed under the water surface during acquisition. This test measures the capacity of the animal to retrieve and retain information learned, which is the location of the platform as a function of the benchmarks outside the pool.

Swimming is recorded using Videotrack software (Viewpoint, Champagne-au-Mont-d'Or, France), with trajectories being analyzed as latencies and distances. The software divides the pool into four quadrants.

Spatial Working memory is specifically assayed by changing the platform location every day and by using a training inter trial interval of 2 min. Training consists in four swims per day during 3 days, with 2 min inter-trial intervals. Start positions, set at each limit between quadrants, is be randomly selected and each animal is allowed a 90 s swim to find the platform. Once it has found it, the animal is left on it during 20 s. The mean latency is calculated over the 3 days for each swim trial. It is indicative of the learning and spatial short memory performances of the animal.

Positive results are noticed concerning the performances of spatial working memory of animals treated with compositions of the invention.

3) Improvement in Long Term Memory:

a) Place Learning in the Water-Maze (Reference Memory, [33])

Animal husbandry and scheme of drugs administration is the same as previously detailed. The water-maze is a circular pool (diameter 140 cm, height 40 cm). The water temperature (23±1° C.), light intensity, external cues in the room (sink, contrasted posters, shelves), and water opacity (obtained using suspension of lime carbonate) is rigorously reproduced. Four departure positions are defined at the cardinal points of the pool (N, E, S, W). A transparent Plexiglas non-slippery platform (diameter 10 cm) could be immersed under the water surface during acquisition. It is placed in the center of the NW quadrant during all the reference memory procedure. Training consists in three swims per day for 5 days with 20 min inter-trial time. Animals are tested by batch of 10 individuals (corresponding to one cage). Start positions are randomly selected each day and animals are allowed a 90 s swim to find the platform. Swimming durations are measured using a stopwatch. Once it has found it, animal is left on the platform during 20 s. If the animal does not reach the platform within 90 s, it will be gently placed on it and remains on it for 20 s. The median latency will be calculated for each training day and expressed as mean±S.E.M. for the whole treatment group.

In order to determine the learning and long term-memory performances of the animals, a probe test is performed 24 h after the last swim. The platform is removed and each animal is allowed a free 60 s swim. They received a spot of black nontoxic stain on the head to be detected by videotracking. Swimming is recorded using Videotrack software (Viewpoint, Champagne-au-Mont-d'Or, France), with trajectories being analyzed as latencies and distances. The software divides the pool into four quadrants according to the start positions. Each mouse starts from one of the two positions remote from the platform location in counterbalanced order. The time spent in each quadrant is determined. The time spent in the quadrant which contained the platform during acquisition is a measure of long term memory performance of the animals.

An improvement of long term memory is observed for the compositions of the invention. (table 6).

TABLE 6

| Animals dosed with: | Enhancement of time spent in the quadrant having contained the plateform |
|---|---|
| Baclofen and acamprosate | + |
| Baclofen and torasemide | + |
| Mexiletine and cinaclacet | + |
| Sulfisoxazole and torasemide | + |
| Vehicle | − |

+: time is enhanced;
−: time is not enhanced b) Step Through Latency Test.

The step through latency test is a fear-aggravated test used to evaluate learning and memory. In this test, subjects learn to avoid an environment in which an aversive stimulus (such as a foot-shock) was previously delivered. As the retention test is performed 24 hours after the training (learning) session, it is an indicator of long term memory performance of the animals.

The apparatus is a two-compartment (15×20×15 cm high) box with one illuminated with white polyvinylchloride walls and the other darkened with black polyvinylchloride walls and a grid floor. A guillotine door separates each compartment. A 60 W lamp positioned 40 cm above the apparatus lights up the white compartment during the experiment. Scrambled footshocks (0.3 mA for 3 s) could be delivered to the grid floor using a shock generator scrambler (Lafayette Instruments, Lafayette, USA). The guillotine door is initially closed during the training session. Each mouse is placed into the white compartment. After 5 s, the door raises. When the mouse enters the darkened compartment and places all its paws on the grid floor, the door closes and the footshock is delivered for 3 s. The step-through latency, that is, the latency spent to enter the darkened compartment, and the number of vocalizations is recorded. The retention test is carried out 24 h after training. Each mouse is placed again into the white compartment. After 5 s the doors is raised, the step-through latency and the escape latency, i.e. the time spent to return into the white compartment, are recorded up to 300 s.

The latency to enter the darkened compartment is interpreted as a measure of learning and memory capabilities of the animal.

c) Results.

Positives results are observed for the baclofen and acamprosate treated animals, showing that compositions of the invention are efficient in improving long term memory.

B. Memory Improvement During Drug Induced Amnesia.

Drug-induced amnesia is provoked by injection of a strongly amnestic drug, scopolamine, to mice. This drug induced a transient amnesia: memories during the active window of the drug are permanently lost or at least substantially reduced, but once the drug wears off, memory is no longer affected.

The ability of the compositions of the invention to protect short term memory against scopolamine induced amnesia was tested, in a % of alternation T maze test, essentially as described above, with 4-5 weeks old CD-1 mice.

Figure 3:
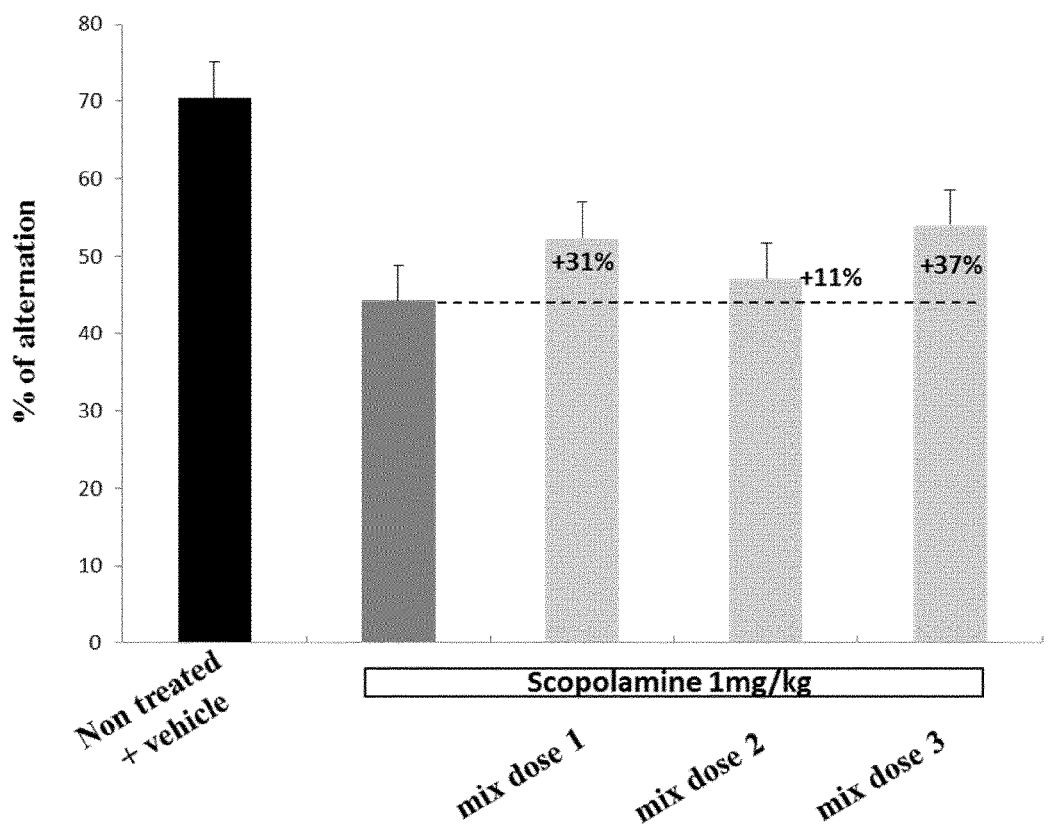
FIG. 3: Compositions of the invention improve learning and working memory performance in scopolamine induced amnesia model, in a chronic scheme (7 days of treatment before the test) of dosing. Memory loss is prevented from 11% to 37% (light grey bars) compared to vehicle dosed, scopolamine treated animals (dark grey bar). Black bar: vehicle dosed animals.
Figure 4:
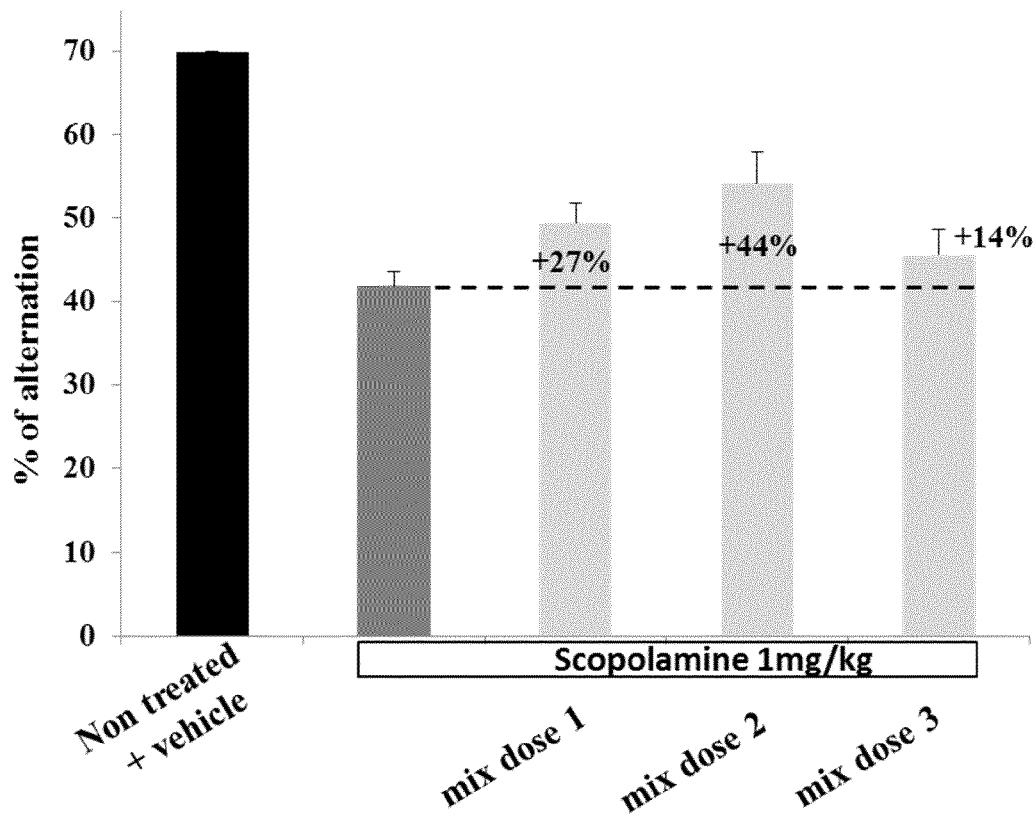
FIG. 4: Improvement of memory performance in scopolamine induced amnesia. Working memory is significantly increased in animals treated only from the eve of the test, when compare to vehicle dosed, scopolamine treated animals (dark grey bar). Loss in learning and memory performances in scopolamine treated animals is reduced from 14% to 44% when they are dosed with baclofen-acamprosate combinations (light grey bars). Black bar: vehicle dosed animals.

The test was performed to evaluate the protective effect of combinations toward induced amnesia for a chronic (FIG. 3, twice a day for 7 days and 2 hours before the test) and a shorter preventive dosage (twice the day before and 2 h before the test; FIG. 4).

Scopolamine is prepared in saline at a concentration of 0.1 mg/mL and injected ip at a dosage volume of 10 ml/kg. This yields a dose of 1 mg/kg. This dose refers to the dose of salt (i.e. scopolamine hydrochloride) form of the drug, and not to the doses of the named molecule per se.

The day of the test, animals are dosed with the drug combinations of the invention, 2 hours before the test. 30 min before performing the test, scopolamine is administered to the animals.

Results

The percent spontaneous alternation is calculated as previously stated. Results are reported in table 7 below and FIGS. 3 and 4.

TABLE 7

| Scopolamine treated animals dosed with: | Improvement in spontaneous alternation |
|---|---|
| Baclofen and acamprosate | + |
| Baclofen and torasemide | + |
| Mexiletine and cinacalcet | + |
| Sulfisoxazole and torasemide | + |
| Vehicle | − |

+: improvement;
−: no improvement.

Results show that the combinations of the invention are efficient in increasing the performance of animals treated with scopolamine and dosed either chronically (table 7, FIG. 3) or from the day before induction of amnesia (table 7, FIG. 4).

Moreover an improvement of performance is noticed for all the tested concentration of baclofen-acamprosate combination.

II. Memory and Cognitive Tests in Human Subjects

Compositions of the invention are efficient in improving memory in healthy human subjects. Baclofen and acamprosate combination efficacy in improving memory or memory related mental functions is currently assessed through a clinical trial. The study is performed in accordance with the European Medicines Agency ICH-E6 (R1) guideline recommendations and the French law n° 2004-806, Aug. 9, 2004 relative to public health law.

A. Measurement of the Cognitive Function in Healthy Subjects.

The study is conducted on a cohort of 12 young healthy male volunteers aged from 18 to 45 years (the "young cohort"). The cohort is randomized in order to have 8 subjects under active drugs and 4 subjects under placebo.

A cohort of 4 elderly subjects (the "elderly cohort") administered with placebo is used to validate experimental settings.

1) Dosage Schedule

The duration of treatment was of 10 days. Baclofen and acamprosate are given orally concomitantly as a combination therapy.

Though tested herein at low doses compared to the usual therapeutic doses, an up-titration dosing schedule is desirable, to increase progressively the dose of baclofen to be daily delivered and thus to limit the possible baclofen induced side effects even they are unlikely.

Then as dosage regimen, each subject is administered the following treatment by oral route:

Day −1: no drug nor placebo administration
Day 1: 6 mg baclofen and 0.4 mg acamprosate, or placebo, in the morning
Day 2: 6 mg baclofen and 0.4 mg acamprosate, or placebo, twice daily (morning and evening)
Day 3: 6 mg baclofen and 0.4 mg acamprosate, or placebo, in the morning and 12 mg baclofen and 0.8 mg acamprosate, or placebo, in the evening
Day 4: 12 mg baclofen and 0.8 mg acamprosate, or placebo, twice daily (morning and evening)
Day 5 to Day 9: 15 mg baclofen and 1 mg acamprosate, or placebo, twice daily (morning and evening)
Day 10: 15 mg baclofen and 1 mg acamprosate, or placebo, in the morning.

2) Cognitive Tests and Electrophysiological Measurements.

Tests presented below allow evaluating effect of compositions of the invention on the memory of the subjects. Four cognitive tests developed by Cogstate® and electrophysiological measurement of Cognitive Event-Related Potentials (ERPs) are used through this trial. These tests were performed on Day −1 (free of drug and placebo administration), Day 1 (at 6 hours post-dose), Day 9 (pre-dose) and Day 10 (at 6 hours post-dose). Concerning cognitive tests, results are expressed as the mean change of the performance between baseline and each time point of a study. Such tests can easily be performed on a personal computer.

a) Assessment of Vigilance and Visual Attention Performances: Identification Test.

The pre-task on-screen instructions ask: "Is the card red?" The test supervisor reads full instructions to the subject from the test supervisor script. To begin the task, the test supervisor or subject must press the "Enter" key. A playing card is presented in the centre of the screen. The card will flip over so it is face up. As soon as it does this the subject must decide whether the card is red or not. If it is red they should press "Yes", if it is not red they should press "No".

The subjects practice until they reach the required number of responses, or until the practice period expires. Then, on screen instructions for the real test are presented. The test supervisor or subject must press the "Enter" key to begin the real test.

The subjects are encouraged to work as quickly as they can and to be as accurate as they can. For example, subjects should try not to press either the "Yes" or "No" key before a card flips over. If they make a mistake they will hear an error sound. The percentage of correct responses is determined.

b) Visual Learning and Memory: One Card Learning Test.

The pre-task on-screen instructions ask: "Have you seen this card before in this task?" The test supervisor reads full instructions to the subject from the test supervisor script. To begin the task, the test supervisor or subject must press the "Enter" key. A playing card is presented in the centre of the screen. As soon as it does the subject must decide whether or not the same card has been seen before in this task. Therefore the first answer is always "No".

Each time a card is revealed, the subjects must decide whether they have been shown that card before in this task and respond by pressing the "Yes" or "No" key. If an incorrect response is given (e.g., "No" is pressed when a card has been presented before) an error noise is heard.

Once the practice is complete (required number of responses or time out reached) the on-screen instructions and the test supervisor tells the subject that the real test is now beginning. The test supervisor or subject must press the "Enter" key to begin the real test.

The subject is encouraged to work as quickly as he can and to be as accurate as he can. For example, he should try not to press either the "Yes" or the "No" key before a card turns over, and he should try and remember all the cards that are presented in this task. If he makes a mistake he will hear an error sound.

The percentage of correct responses is determined.

c) Psychomotor Functions and Speed of Processing: Detection Task (DET).

The pre-task on-screen instructions ask: "Has the card turned over?" The test supervisor reads full instructions to the subject from the test supervisor script. To begin the task, the test supervisor or subject must press the "Enter" key. A playing card is presented in the centre of the screen. The card will flip over so it is face up. As soon as it does, the subject must press the "Yes" key. The card will go to the back of the pack and the subject must press the "Yes" key as soon as the next card flips over and so on.

The subject practices until they reach the required number of responses, or until the practice period expires. Then, on screen instructions for the real test are presented. The test supervisor or subject must press the "Enter" key to begin the real test.

The subject is encouraged to work as quickly as he can and to be as accurate as he can. For example, he should try not to press the "Yes" key before a card flips over. If the subject does this or does not respond to a card that has flipped over in time, he will hear an error sound.

Results are expressed as a mean of speed of performance (Lmn, mean of the Log 10 transformed reaction times for correct responses).

d) Executive Function and Spatial Problem Solving: Groton Maze Learning Task (GMLT).

The subject is shown a 10×10 grid of tiles on a computer touch screen. A 28-step pathway is hidden among these 100 possible locations. The start is indicated by the blue tile at the top left and the finish location is the tile with the red circles at the bottom right of the grid. The subject is instructed to move one step from the start location and then to continue, one tile at a time, toward the end (bottom right).

The subject moves by touching a tile next to their current location with the stylus. After each move is made, the computer indicates whether this is correct by revealing a green checkmark (i.e. this is the next step in the pathway), or incorrect by revealing a red cross (i.e. this is not the next step in the pathway, or the subject has broken a rule, see below). If a choice is incorrect (i.e. a red cross is revealed), the subject must touch the last correct location (i.e. the last green checkmark revealed) and then make a different tile choice to advance toward the end.

While moving through the hidden maze, the subject is required to adhere to two rules. Firstly, the subject cannot move diagonally or touch the same tile twice in succession. Secondly, the subject cannot move backwards along the pathway (e.g., move back to a location that displayed a green tick, but from which they have since moved on from).

If the subject chooses a tile that is not part of the hidden pathway, but the tile choice is within the rules, this is recorded as a different type of error (e.g. not a rule break). This could be due to chance (the first time through the maze) or due to misremembering the path on subsequent attempts.

The subject learns the 28-step pathway though the maze on the basis of this trial and error feedback. Once completed, they are returned to the start location and repeat the task, usually 4 more times, trying to remember the pathway they have just completed.

There are 20 well-matched alternate forms for this task, and these are selected in pseudo-random order to ensure that no subject will complete the same hidden path on any two different testing sessions throughout a study.

The criteria which are measured by the means of GMLT test, for the present study are:
the efficiency of performance: mps
the duration of task: dur
the total number of errors: ter
   per (perseveration)
   rer (rule break errors)
   ler (legal numbers of errors)
number of correct moves: cmv
return to head errors: rth The data from these 4 cognitive tests (cf. a, b, c, d) are analyzed each independently or pooled together in a "composite" Cogstate® score.

e) Sensory Event Reflecting Attention: Event-Related Potentials (ERPs).

ERPs have a large application in the evaluation of cognitive processes because results are independent from the stimulus which is used and because they provide information on stimulus processing even when no behavioural change is perceptible. They are often considered as the more unbiased tests when compared to behavioural cognitive tests.

Records from three scalp derivations (frontal: Fz, central: Cz, parietal: Pz) are gathered according to the international 10/20 standards, with, as a reference, two linked electrodes attached to the right and left earlobes (A1-A2). The cognitive task requires paying attention to the odd stimuli and counting them according to a specific protocol.

The subject is submitted to a random sequence of sound stimuli and ERPs measure the P300 wave elicited by oddballs (with N200 and P300 subcomponents latency and amplitude) which reflects attention. Subjects with an impaired cognition show delayed signals of lower amplitude.

The score summarizing data for these three derivations is given as the ERP "composite" score.

3) Results a) Validation Study.

Figure 5:
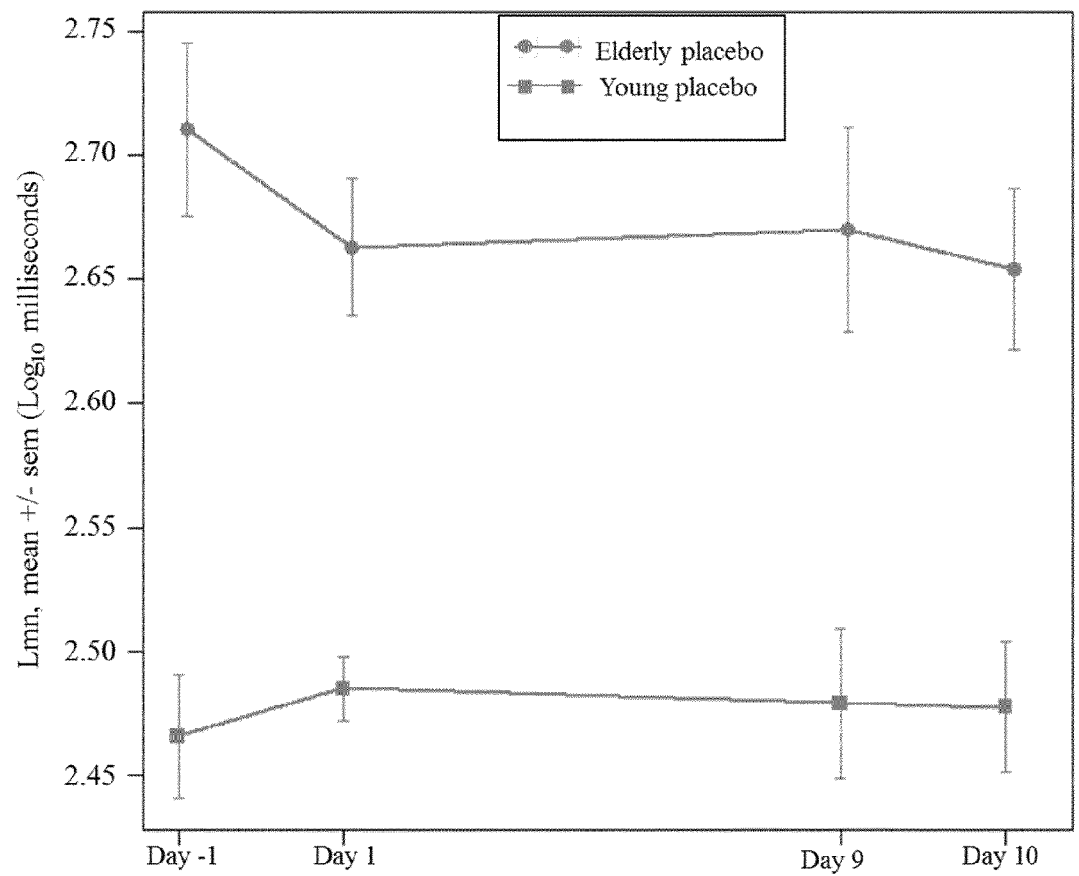
FIG. 5: Young subjects perform better than the elderly in detection task test (DET). Scores raw data in DET (Lmn, Speed of performance) of young cohort (full squares) and of elderly cohort (full circles), both administered with placebo are plotted as a function of experimental time schedule. Best performances result in lowest scores. As expected, cognitive performances in young subjects are higher than in elderly.

Experimental settings of cognitive behavioral tests were checked by comparing the results obtained in the non-treated elderly and young cohorts. A clear difference in cognitive performances between the young cohort and the elderly cohort is noticed as illustrated in the DET test presented in FIG. 5. The young cohort shows higher cognitive performances comparing to the elderly cohort, which is consistent with the normal age-related cognitive decline.

b) Combinations of the Invention are Efficient in Improving Cognitive Performance in Healthy Young Subjects.

Improvements of Performances in Cognitive Tests.

Figure 6:
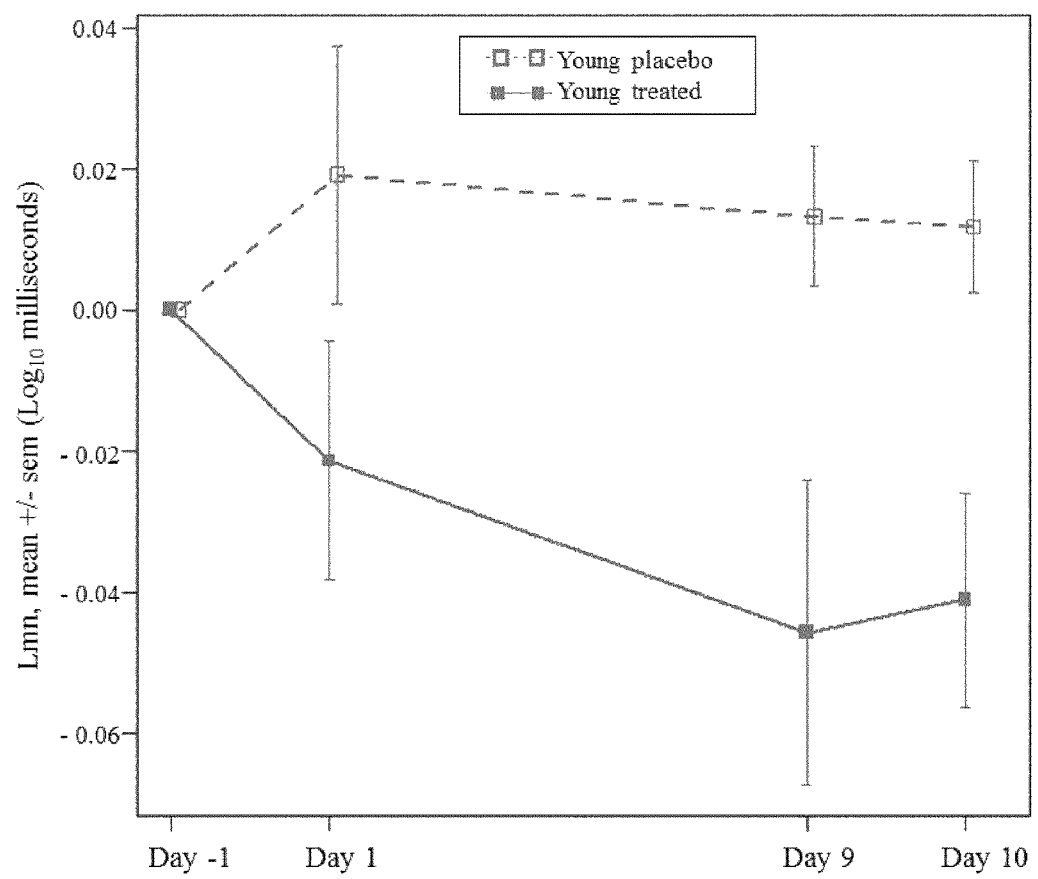
FIG. 6: Baclofen-acamprosate combination improves cognitive functions of healthy subjects. Scores in change from baseline in DET (Lmn, Speed of performance, a decrease corresponds to an improvement of performances) in young cohort administered with baclofen-acamprosate (full squares, full line) or with placebo (open squares, dotted line) are plotted as a function of experimental time schedule. Subjects administered with baclofen-acamprosate combination perform better than the subjects administered with placebo. The improvement in performances is observed in the treated cohort all long the duration of the treatment.

The combinations of the invention have been found efficient in improving cognitive functions in treated healthy young human subjects when compared to non-treated subjects. Baclofen-acamprosate-treated subjects show an improvement in their cognitive performances as shown in the DET test in FIG. 6; this improvement lasts all along the treatment.

Improvement of Memory and Memory Related Mental Functions is Correlated with Plasmatic Concentrations of Drugs.

Pharmacodynamics of baclofen and acamprosate have been established in the frame of clinical trial. "Time of occurrence of maximum plasma concentration" (Tmax) has been determined as occurring at 1.5-2 hours after administration for acamprosate and 1.5 hours for baclofen. Hence one can consider that Tmax of the combination is 1.5-2 hours after concomitant administration of each drug.

Figure 7:
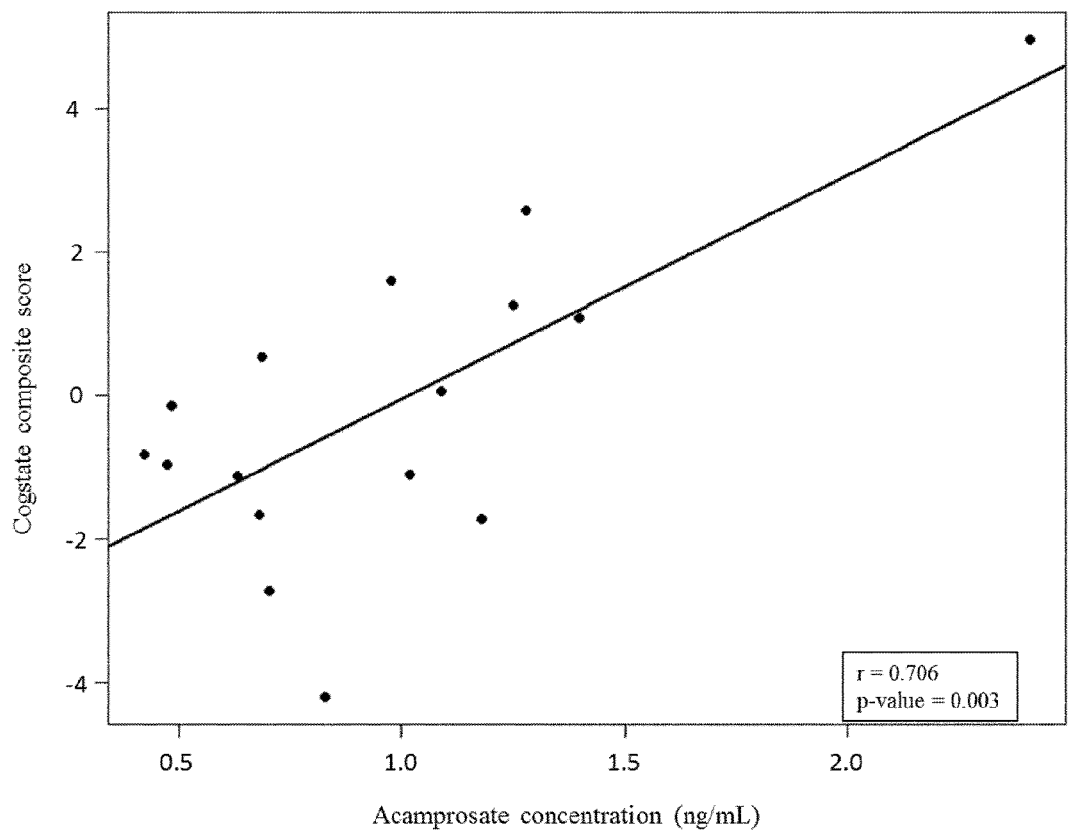
FIG. 7: Performances in Cogstate®cognitive tests are correlated with the plasmatic concentration of the mix compounds. A positive correlation (r, Pearson correlation test) between the plasmatic concentrations of acamprosate at Day 10, 5 hours after the drugs administration (horizontal scale) in blood samples from subjects and composite score of cognitive tests at Day 10, 6 hours after the drugs administration (vertical scale) is observed.

At Day 10, the drug combination was administered and Cogstate R tests were performed 6 hours after drug administration. As shown in FIG. 7, a positive and significant correlation (Pearson correlation test) between the plasma concentrations of acamprosate (5 hours after drug administration) with the level of composite Cogstate® score registered in the young cohort is observed (FIG. 7, correlation coefficient=0.706; p-value=0.003).

Figure 8:
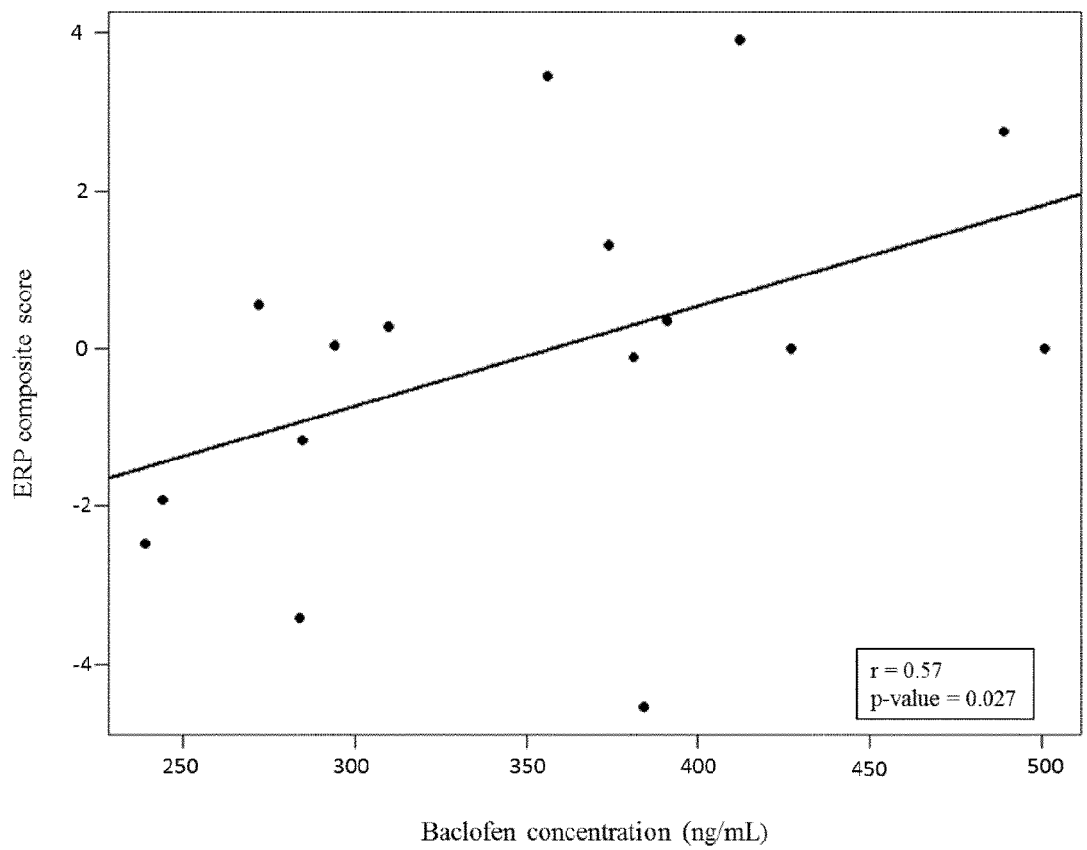
FIG. 8: ERP data are correlated with the plasmatic concentration of the mix compounds. A positive correlation (r, Pearson correlation test) is observed between the plasmatic concentrations of baclofen at Day 10, 1.5 hours after the drugs administration and the ERP composite score at Day 10, 6 hours after the drugs administration.
Figure 9:
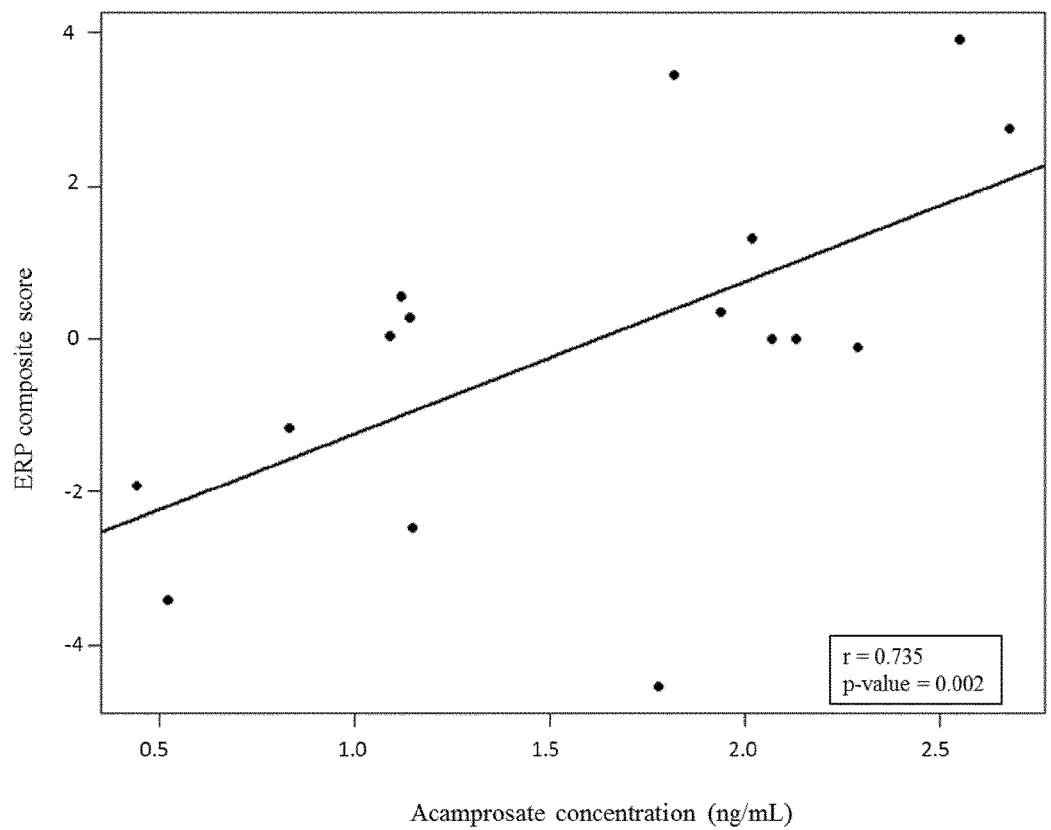
FIG. 9: ERP data are correlated with the plasmatic concentration of the mix compounds. A positive correlation (r, Pearson correlation test) is found between the plasmatic concentrations of acamprosate at Day 10, 1.5 hours after the drugs administration and ERP composite score at Day 10, when ERP measures are gathered 6 hours from drugs administration.

Such a correlation is also observed when looking at electrophysiological component of memory and related mental functions. Indeed, as reported in the FIGS. 8 and 9, a particularly significant correlation between the plasmatic concentrations (Pearson correlation test) of baclofen and acamprosate 1.5 hours after administration (corresponding approximately to the Tmax) with the respective ERP latencies composite score (measured 6 hours after the administration of the drugs) is observed on Day 10: plasma concentration of both drugs are positively correlated with shorter latencies in ERP (for acamprosate, FIG. 9, correlation coefficient=0.735; p-value=0.002; for baclofen, FIG. 8, correlation coefficient=0.57; p-value=0.027). Subjects performing the best are those for which the higher plasmatic concentration is observed at 1.5 hours.

These correlations emphasize the fact that the improvement in cognitive performances of treated healthy young subjects is actually related to the compositions of the invention.

Hence, the above results show the efficacy of baclofen and acamprosate combination in improving cognitive performances in healthy young subject.

B. Improvement in Memory and Related Functions in Humans Subjected to Chemically Induced Cognitive Impairment.

Scopolamine induced cognitive decline is the model used to mimic the cognitive deficits that may be induced when exposed to several substances. As stated above for the animals, this drug induces a transitory and reversible cognitive impairment when administered to volunteers [34].

Cognitive performances of the subjects are tested using the Cognitive Groton Maze Learning Task Test as explained in part A.

1) Dosage Schedule.

Twenty young healthy male volunteers aged 20 to 45 years are enrolled in the study.

A randomized, 2-way cross-over, double blind, placebo-controlled study is performed. The study has two distinct parts each consisting in 40 hours hospitalization and being spaced from each other by 7 days as a wash out period. Baclofen and acamprosate are administered orally and concomitantly.

As a dose regimen, each subject is administered according the following treatment by oral route:

Each subject receives the baclofen (6 mg) and acamprosate (0.4 mg) mix or placebo, orally, in a sub-acute administration, b.i.d on Day 1 and in a single dose on the test day (Day 2) at H3, before scopolamine injection.

At Day 2, H3, a sub-cutaneous injection of 0.5 mg of scopolamine is performed.

2) Experimental design.

Effects on impaired cognition are explored by measuring the following features in the GMLT test:

the efficiency of performance: mps the total number of errors: ter the duration of task: dur Cognitive Groton Maze Learning Task Test is performed on Day 1 (training), and on Day 2 H0, H2.5, H4, H5.5, H7 and H9 and Day 3 H24.

3) Baclofen and Acamprosate Combination Improves the Cognitive Deficit Induced by Scopolamine.

Similar data are obtained for each of mps, ter and dur component of the GMLT test. The data from Groton Maze Learning Test (GMLT) are pooled together in a "composite" GMLT score which is presented in FIG. 10.

Figure 10:
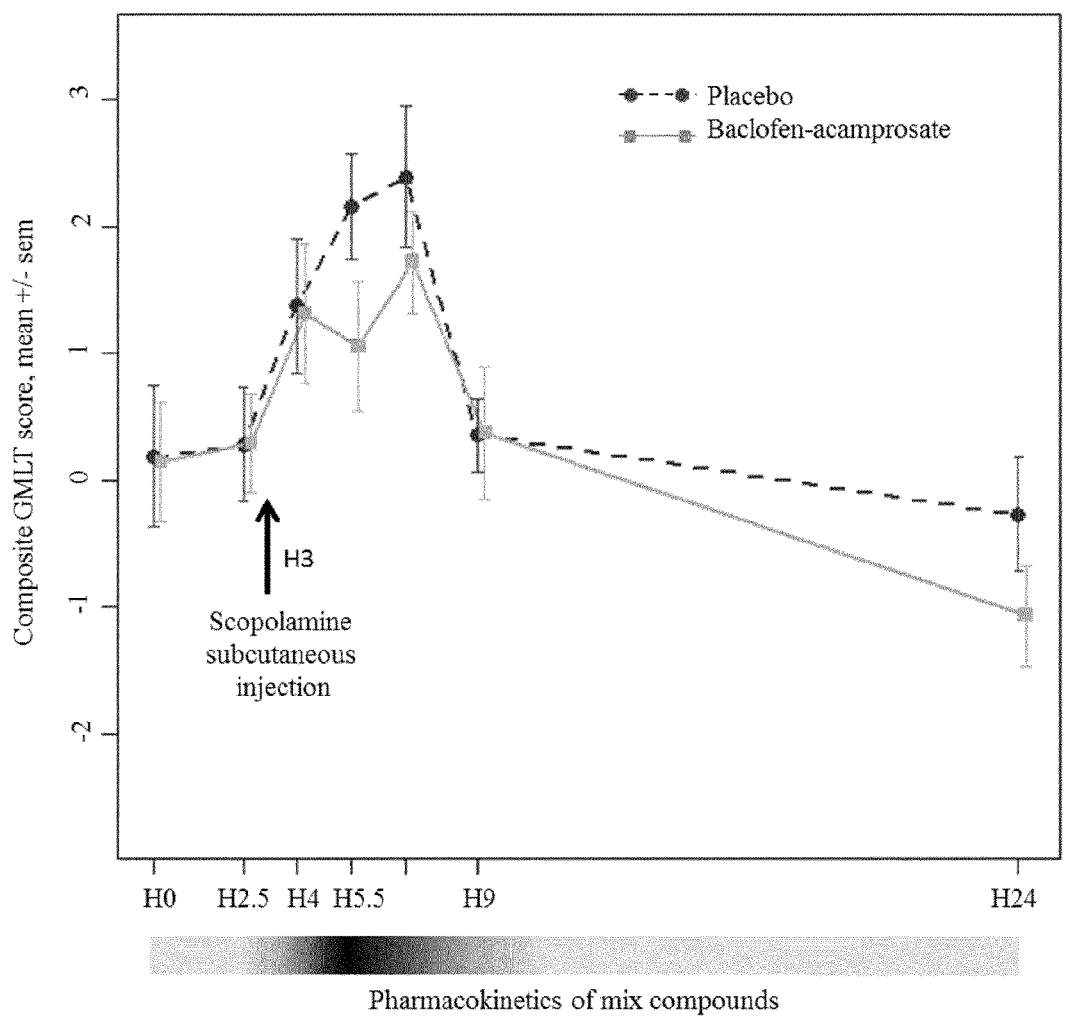
FIG. 10: Baclofen-acamprosate combination efficiently reduces scopolamine induced cognitive impairments. Score raw data in Groton Maze Learning Test (GMLT) are plotted along vertical scale. An increase in the score corresponds to an impairment of performances in GMLT. Scopolamine (administered at H3) induces a rapid decrease in cognitive performances in placebo-treated subjects (circles, dotted line) which lasts for approximately 6 hours (H9) after scopolamine injection. Baclofen-acamprosate mix (squares, grey line) is efficient over this period in reducing deleterious effects of scopolamine on the cognitive performances. A significant improvement of cognitive score is observed in the time window corresponding to the higher plasmatic concentrations of baclofen and acamprosate (shaded bar below the horizontal scale, dark: higher plasmatic concentrations, light: lower plasmatic concentrations).

Scopolamine is known to act as early as 30 min after its administration, its effect lasting for approximately 6 hours. Its Tmax is known to be of about 3 hours [34]. These data correspond to the transient collapse of performances in the GMLT test observed in the non-treated subjects (FIG. 10, circles, dotted line).

An improvement of cognitive performances is observed for baclofen-acamprosate treated subjects compared to placebo dosed subjects. This improvement is particularly significant in the time period around H5.5 that corresponds to the Tmax of baclofen and acamprosate (FIG. 10, grey area).

Hence, baclofen and acamprosate combination is efficient in counteracting scopolamine induced cognitive impairment.

Combinations of the invention are thus efficient in reversing memory impairment resulting from the exposition to the memory impairing toxics or drugs.

REFERENCES

1 Lanni C, Lenzken S C, Pascale A, Del Vecchio I, Racchi M, Pistoia F & Govoni S (2008) Cognition enhancers between treating and doping the mind. *Pharmacological research: the official journal of the Italian Pharmacological Society* 57, 196-213.

2 Balaraman (2002) Nootropics. *Indian Journal of Pharmacology* 34, 439.

3 Sahakian B J & Morein-Zamir S (2011) Neuroethical issues in cognitive enhancement. *Journal of psychopharmacology* (Oxford, England) 25, 197-204.

4 Dimond S J & Brouwers E M (1976) Increase in the power of human memory in normal man through the use of drugs. *Psychopharmacology* 49, 307-9.

5 Noorbala A A, Akhondzadeh S, Davari-Ashtiani R & Amini-Nooshabadi H (1999) Piracetam in the treatment of schizophrenia: implications for the glutamate hypothesis of schizophrenia. *Journal of clinical pharmacy and therapeutics* 24, 369-74.

6 Hofmann S G, Fang A & Gutner C A (2013) Cognitive enhancers for the treatment of anxiety disorders. *Restorative neurology and neuroscience*.

7 Cho Y W, Kim D H & Motamedi G K (2011) The effect of levetiracetam monotherapy on subjective sleep quality and objective sleep parameters in patients with epilepsy: compared with the effect of carbamazepine-C R monotherapy. *Seizure: the journal of the British Epilepsy Association* 20, 336-9.

8 Pinto A & Sander J W (2003) Levetiracetam: a new therapeutic option for refractory epilepsy. *International journal of clinical practice* 57, 616-21.

9 Milner C A, Schafer M, Schneider S, Heimann H M, Hinzpeter A, Volkmar K, Forg A, Heinz A & Hein J (2010) Efficacy and safety of levetiracetam for outpatient alcohol detoxification. *Pharmacopsychiatry* 43, 184-9.

10 Kondoh T, Kanno A, Itoh H, Nakashima M, Honda R, Kojima M, Noguchi M, Nakane H, Nozaki H, Sasaki H, Nagai T, Kosaki R, Kakee N, Okuyama T, Fukuda M, Ikeda M, Shibata Y & Moriuchi H (2011) Donepezil significantly improves abilities in daily lives of female Down syndrome patients with severe cognitive impairment: a 24-week randomized, double-blind, placebo-controlled trial. *International journal of psychiatry in medicine* 41, 71-89.

11 Stackman R W & Walsh T J (1994) Baclofen produces dose-related working memory impairments after intraseptal injection. *Behavioral and neural biology* 61, 181-5.

12 Grande L A, Loeser J D & Samii A (2008) Recurrent transient global amnesia with intrathecal baclofen. *Anesthesia and analgesia* 106, 1284-7, table of contents.

13 Schneider U, Wohlfarth K, Schulze-Bonhage A, Haacker T, Müller-Vahl K R, Zedler M, Becker H, Dengler R & Emrich H M (1999) Effects of acamprosate on memory in healthy young subjects. *Journal of studies on alcohol* 60, 172-5.

14 Tannenbaum C, Paquette A, Hilmer S, Holroyd-Leduc J & Carnahan R (2012) A systematic review of amnestic and non-amnestic mild cognitive impairment induced by anticholinergic, antihistamine, GABAergic and opioid drugs. *Drugs & aging* 29, 639-58.

15 Ettmayer P, Amidon G L, Clement B & Testa B (2004) Lessons learned from marketed and investigational prodrugs. *Journal of medicinal chemistry* 47, 2393-404.

16 Beaumont K, Webster R, Gardner I & Dack K (2003) Design of ester prodrugs to enhance oral absorption of poorly permeable compounds: challenges to the discovery scientist. *Current drug metabolism* 4, 461-85.

17 Heimbach T, Oh D M, Li L Y, Rodriguez-Hornedo N, Garcia G & Fleisher D (2003) Enzyme-mediated precipitation of parent drugs from their phosphate prodrugs. *International journal of pharmaceutics* 261, 81-92.

18 Yang C Y, Dantzig A H & Pidgeon C (1999) Intestinal peptide transport systems and oral drug availability. *Pharmaceutical research* 16, 1331-43.

19 Steffansen B, Nielsen C U, Brodin B, Eriksson A H, Andersen R & Frokjaer S (2004) Intestinal solute carriers: an overview of trends and strategies for improving oral drug absorption. *European journal of pharmaceutical sciences: official journal of the European Federation for Pharmaceutical Sciences* 21, 3-16.

20 Stella V J (2007) *Prodrugs: challenges and rewards*. Springer Singapore Pte. Limited.

21 Wermuth C G (2011) *The Practice of Medicinal Chemistry* Elsevier Science.

22 Pezron I, Mitra A K, Duvvuri S & Tirucherai G S (2002) Prodrug strategies in nasal drug delivery. *Expert Opinion on Therapeutic Patents* 12, 331-340.

23 Stella V J (2004) Prodrugs as therapeutics. *Expert Opinion on Therapeutic Patents* 14, 277-280.

24 Stella V J & Nti-Addae K W (2007) Prodrug strategies to overcome poor water solubility. *Advanced drug delivery reviews* 59, 677-94.

25 Roche E B (1977) *Design of biopharmaceutical properties through prodrugs and analogs: a symposium*, American P The Academy, Washington, D.C.

26 Lal R, Sukbuntherng J, Tai E H L, Upadhyay S, Yao F, Warren M S, Luo W, Bu L, Nguyen S, Zamora J, Peng G, Dias T, Bao Y, Ludwikow M, Phan T, Scheuerman R A, Yan H, Gao M, Wu Q Q, Annamalai T, Raillard S P, Koller K, Gallop M A & Cundy K C (2009) Arbaclofen placarbil, a novel R-baclofen prodrug: improved absorption, distribution, metabolism, and elimination properties compared with R-baclofen. *The Journal of pharmacology and experimental therapeutics* 330,911-21.

27 Xu F, Peng G, Phan T, Dilip U, Chen J L, Chernov-Rogan T, Zhang X, Grindstaff K, Annamalai T, Koller K, Gallop M A & Wustrow D J (2011) Discovery of a novel potent GABA(B) receptor agonist. *Bioorganic & medicinal chemistry letters* 21, 6582-5.

28 Leach A R & Gillet V J *An Introduction to Chemoinformatics* (Springer-Verlag New York Inc, ed.).

29 Rahman S A, Bashton M, Holliday G L, Schrader R & Thornton J M (2009) Small Molecule Subgraph Detector (SMSD) toolkit. *Journal of cheminformatics* 1, 12.

30 Stahl P H & Wermuth C G (2008) *Pharmaceutical Salts* Wiley.

31 Hanafi R, Mosad S, Abouzid K, Niess R & Spahn-Langguth H (2011) Baclofen ester and carbamate prodrug candidates: a simultaneous chromatographic assay, resolution optimized with DryLab. *Journal of pharmaceutical and biomedical analysis* 56, 569-76.

32 DEMBER W N & FOWLER H (1958) Spontaneous alternation behavior. *Psychological bulletin* 55, 412-28.

33 De Bruin N M W J, Prickaerts J, Lange J H M, Akkerman S, Andriambeloson E, De Haan M, Wijnen J, Van Drimmelen M, Hissink E, Heijink L & Kruse C G (2010) SLV330, a cannabinoid CB1 receptor antagonist, ameliorates deficits in the T-maze, object recognition and Social Recognition Tasks in rodents. *Neurobiology of learning and memory* 93, 522-31.

34 Snyder P J, Bednar M M, Cromer J R & Maruff P (2005) Reversal of scopolamine-induced deficits with a single dose of donepezil, an acetylcholinesterase inhibitor. *Alzheimer's & dementia: the journal of the Alzheimer's Association* 1, 126-35.

The invention claimed is:

1. A method for improving memory or memory related mental function performances in a subject, comprising administering to said subject an effective amount of (a) at least two compounds selected from the group consisting of baclofen, acamprosate, cinacalcet, mexiletine, sulfisoxazole, and torasemide, or (b) salt(s) or sustained release formulation(s) thereof, wherein said subject is not experiencing a condition which impairs his memory or memory related mental function performances.

2. The method of claim 1, wherein the memory related mental function performances are selected from the group consisting of learning, reasoning, alertness, attention, concentration, and language processing.

3. The method of claim 1, wherein the memory is short-term memory or long-term memory.

4. The method of claim 1, wherein the subject is administered:
   baclofen and acamprosate,
   mexiletine and cinacalcet,
   baclofen and torasemide,
   sulfisoxazole and torasemide, or
   salt(s) or sustained release formulation(s) thereof.

5. The method of claim 1, which comprises administering at least one further compound selected from the group consisting of methimazole, prilocaine, dyphylline, quinacrine, carbenoxolone, aminocaproic acid, cabergoline, diethylcarbamazine, cinacalcet, cinnarizine, eplerenone, fenoldopam, leflunomide, levosimendan, sulodexide, terbinafine, zonisamide, etomidate, phenformin, trimetazidine, mexiletine, ifenprodil, moxifloxacin, bromocriptine, torasemide, and donepezil.

6. The method of claim 1, which further comprises administering a racetam selected from levetiracetam, piracetam, pramiracetam, aniracetam or oxiracetam.

7. The method of claim 1, wherein said compounds are formulated with a pharmaceutically acceptable carrier or excipient.

8. The method of claim 1, wherein the compounds are formulated or administered together, separately or sequentially.

9. The method of claim 8, wherein the compounds are formulated together in one composition.

10. The method of claim 1, wherein said compounds are administered repeatedly to said subject.

11. The method of claim 1, wherein said subject has a need for a transient stimulation in memory, learning, or alertness performance.

12. The method of claim 1, wherein said subject exhibits transient memory loss caused by hormonal changes or imbalances.

* * * * *